United States Patent
Allred et al.

(10) Patent No.: US 7,011,523 B2
(45) Date of Patent: *Mar. 14, 2006

(54) BLEACHING COMPOSITIONS AND DEVICES HAVING A SOLID ADHESIVE LAYER AND BLEACHING GEL ADJACENT THERETO

(75) Inventors: Peter M. Allred, Riverton, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/692,117

(22) Filed: Oct. 22, 2003

(65) Prior Publication Data

US 2005/0089819 A1   Apr. 28, 2005

(51) Int. Cl.
*A61C 5/00* (2006.01)
*A61C 17/02* (2006.01)

(52) U.S. Cl. ........................................ 433/215; 433/80
(58) Field of Classification Search .................. 433/80, 433/215, 216; 424/53; 206/63.5, 369
See application file for complete search history.

(56) References Cited

U.S. PATENT DOCUMENTS

| | | | |
|---|---|---|---|
| 165,584 A | 7/1875 | Hopfen | |
| 1,637,153 A | 7/1927 | Lawton | |
| 2,257,709 A | 9/1941 | Anderson | 128/260 |
| 2,835,628 A | 5/1958 | Saffir | 167/84 |
| 3,339,547 A | 9/1967 | Drabkowski | 128/260 |
| 3,527,219 A | 9/1970 | Greenberg | 128/260 |
| 3,577,640 A | 5/1971 | Lee | 32/32 |
| 3,624,909 A | 12/1971 | Greenberg | 32/40 |
| 3,688,406 A | 9/1972 | Porter et al. | 32/40 R |
| 3,955,281 A | 5/1976 | Weitzman | 32/14 B |

(Continued)

FOREIGN PATENT DOCUMENTS

| | | |
|---|---|---|
| WO | WO 88/06869 | 9/1988 |
| WO | WO 03/000216 | 1/2003 |

OTHER PUBLICATIONS

Technical Bulletin: Hydrogen Peroxide–Polyvinylpyrrolidone Polymer Complexes, International Specialty Products, 1361 Alps Road, Wayne New Jersey 07470, www.ispcorp.com (Dec. 2003).

*Primary Examiner*—Cary E. O'Connor
(74) *Attorney, Agent, or Firm*—Workman Nydegger

(57) ABSTRACT

Dental bleaching compositions in the shape of a dental tray or tray-like form include a substantially solid adhesive layer and a dental bleaching gel. A barrier layer may be included on an outer surface of the adhesive layer to form a dental bleaching device. The adhesive layer comprises a substantially solid adhesive composition that has increased adhesiveness to oral tissue when moistened with saliva or water. The adhesive layer is formed from an intermediate composition that is heated to drive off the solvent. Using a bleaching gel separate from the adhesive layer improves the potency and stability of the bleaching agent, as the bleaching gel is not heated like the adhesive layer. The shape of the dental bleaching device facilitates placement of the device over a person's teeth with substantially less manipulation compared to the use of initially flat bleaching strips. The moistened adhesive composition reliably adheres the dental bleaching composition or device against a user's teeth during a bleaching procedure. Because a substantial portion of the adhesive composition remains solid or semi-solid during bleaching, the adhesive composition maintains a substantial portion of its adhesive properties and internal cohesive strength compared to, e.g., a bleaching gel used by itself.

60 Claims, 7 Drawing Sheets

U.S. PATENT DOCUMENTS

| | | | |
|---|---|---|---|
| 4,044,762 A | 8/1977 | Jacobs | 128/136 |
| 4,063,552 A | 12/1977 | Going et al. | 128/136 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir | |
| 4,902,227 A | 2/1990 | Smith | 433/215 |
| 5,008,093 A | 4/1991 | Merianos | |
| 5,051,476 A | 9/1991 | Uji et al. | 525/186 |
| 5,085,585 A | 2/1992 | Zimble | 433/80 |
| 5,108,742 A | 4/1992 | Merianos | |
| 5,112,225 A | 5/1992 | Diesso | 433/48 |
| 5,183,901 A | 2/1993 | Login et al. | |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A * | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/691 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A * | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 | 4/2002 | Trettenero | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,649,147 B1 | 11/2003 | Ye et al. | |
| 6,682,721 B1 | 1/2004 | Kim et al. | |
| 6,689,344 B1 | 2/2004 | Chang et al. | |
| 6,730,316 B1 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

* cited by examiner

BLEACHING COMPOSITIONS AND DEVICES HAVING A SOLID ADHESIVE LAYER AND BLEACHING GEL ADJACENT THERETO

BACKGROUND OF THE INVENTION

1. The Field of the Invention

This invention is in the field of dental bleaching compositions and devices used to bleach a person's teeth. More particularly, the invention relates to bleaching compositions and devices in the shape of a dental tray, or having a tray-like configuration, that include a substantially solid adhesive layer that becomes adhesive to teeth when moistened (e.g., by moisture or saliva on a user's teeth), dental bleaching gel adjacent to the solid adhesive layer,: and optionally a moisture-resistant barrier layer adjacent to the adhesive layer.

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray can be expensive.

Because of the time and cost associated with making customized trays, less time consuming and costly alternatives have been developed. Contrary to marketing campaigns, however, many alternatives have substantial disadvantages, primarily in terms of their effectiveness (or ineffectiveness) in actually bleaching teeth. They also have their own unique issues relating to ease of use, comfort and poor taste (bleaching compositions are, after all, placed directly into a person's mouth).

One alternative to customized dental trays are non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental Trays that can be self-customized (e.g., so-called "boil-and-bite" trays) are somewhat more comfortable and better-fitting compared to non-custom trays but less comfortable than trays that are customized by a dentist.

Another alternative tooth bleaching method involves painting a bleaching composition directly onto the surfaces of a person's teeth to be bleached. An advantage of this procedure is that it eliminates the need to obtain a customized tray, or even a non-custom tray. The main disadvantage, however, is that the bleaching composition remains directly exposed to the person's saliva and disruptive forces and movements normally found within a person's mouth. The result is that a significant portion of the bleaching composition does not remain on the tooth where bleaching is desired. Instead, some or all of the composition can dissolve away into the person's saliva and/or be transferred to adjacent oral tissues. Because paint-on dental bleaching compositions, like all dental bleaching compositions, contain peroxide-based bleaching agents, irritation to soft oral tissues within the user's mouth and throat is a potential problem when using such compositions.

Yet another alternative tooth bleaching method involves placing a flexible bleaching strip over a user's tooth surfaces. Bleaching strips typically comprise a flexible plastic strip coated with a moist dental bleaching gel on the side of the strip facing the user's teeth. To install the bleaching strip, a portion of the bleaching strip is first placed over the front surfaces of the user's teeth, followed by folding the remainder of the strip around the occlusal edges of the teeth and back against a portion of the lingual surfaces. Like paint-on bleaching compositions, this procedure does not require the user to obtain a customized tray, or even a non-custom tray, into which a bleaching composition must be placed by the user prior to use. An advantage of bleaching strips over paint-on bleaching compositions is that bleaching strips include a barrier that, at least in theory, protects the dental bleaching gel from diffusing into the user's mouth.

In reality, however, because of the generally poor adhesion of bleaching strips to the user's teeth, coupled with their generally flimsy nature, it is often difficult for the user to maintain the bleaching strips in their proper position. Bleaching strips are prone to slip off the teeth through even minimal movement of the user's mouth, jaw or tongue. Indeed, it is recommended that the user not eat, drink, smoke or sleep while wearing the bleaching strip. In practice, it is difficult to talk while maintaining the bleaching strips properly oriented over the teeth to be bleached.

Even if a user successfully maintains the bleaching, strip in its proper position during the entire bleaching event, the flowable bleaching gel can diffuse into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially exposing a new portion of the bleaching gel that remains adhered to the newly exposed surface of the user's teeth. In some cases, the bleaching strip can become so dislodged or mangled -that it must be removed by the user and replaced with a fresh bleaching strip to complete the recommended bleaching time. This multiplies the cost and hassle of the bleaching strip method.

In practical terms, the use of bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are prone to move the least is at night while the person is sleeping. Unfortunately, it is recommended that bleaching strips not be used while sleeping, presumably to prevent accidental choking on an inadvertently dislodged bleaching strip. This only confirms the tendency of such bleaching strips to easily dislodge from a user's teeth.

Ultimately, the main impediment to successful bleaching is the failure of users to complete the prescribed bleaching regimen. If the bleaching apparatus is difficult to use, requires numerous repetitions to achieve observable results, or is simply uncomfortable or a hassle to wear, the user may simply give up and abort the bleaching process altogether. Thus, even if significant dental bleaching is possible using a particular bleaching product, it is less likely to occur where the inadequacies of the bleaching apparatus or method causes users to become discouraged before desired results are attained.

In view of the foregoing, there is an ongoing need for improved bleaching apparatus and methods that are simple and easy to use, that more reliably remain in position over the user's teeth, and that result in less diffusion of bleaching composition into a user's oral cavity. Such improvements would be expected to improve or encourage compliance by the user.

BRIEF SUMMARY OF THE PREFFERED EMBODIMENTS

The present invention generally relates to improved dental bleaching compositions and devices used to bleach a person's teeth. Dental bleaching compositions according to the invention include an adhesive layer comprising a substantially solid adhesive composition in the form of a dental tray, or having a tray-like configuration, that becomes more adhesive to teeth when moistened (e.g., by saliva or water), and a dental bleaching gel adjacent to the adhesive layer. The dental bleaching gel may comprise a bead, a continuous layer, or a plurality of discontinuous regions or islands.

Dental bleaching devices according to the invention include a moisture-resistant barrier layer, such as a dental tray or thin membrane having no predefined shape, an adhesive layer comprising a substantially solid adhesive composition that becomes more adhesive to teeth when moistened (e.g., by saliva or water) adjacent to the barrier layer, and a dental bleaching gel adjacent to the adhesive layer. The dental bleaching gel may comprise a bead, a continuous layer, or a plurality of discontinuous regions or islands. In the case where the barrier layer is a dental tray, the adhesive layer may be a continuous layer or a plurality of discontinuous regions. In the case where the barrier layer comprises a thin membrane having no predefined shape, the adhesive layer is advantageously shaped like a dental tray or has a tray-like configuration. To the extent that a barrier layer is subsequently applied or attached to an existing dental bleaching composition comprising (i) an adhesive layer and (ii) bleaching gel, the bleaching composition may be considered to be an intermediate to the finished dental bleaching device comprising the bleaching composition and the barrier layer.

The optional barrier layer advantageously comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin, polyester, polyurethane, or similar moisture-resistant material. The barrier layer may comprise a conventional dental tray, examples of which include both customized and non-custom dental trays. The barrier layer may be as simple as a layer of a moisture resistant barrier-forming material that is sprayed or painted on, applied by dipping, or otherwise applied to an existing adhesive layer comprising a substantially solid adhesive composition (e.g., one that is in the form of a dental tray or that otherwise has a desired shape).

The substantially solid adhesive composition forming the adhesive layer comprises at least one tooth adhesion agent that contributes or provides increased adhesiveness to teeth when moistened by saliva or water, and optionally at least one active agent. When placed over a person's teeth, the adhesive composition reliably adheres to the teeth, thereby maintaining reliable contact between the dental bleaching gel and a person's teeth to be bleached. A barrier layer is advantageously provided to protect the adhesive layer and bleaching gel from diffusing away from the person's teeth into the oral cavity as a result of ambient saliva or moisture found within the person's mouth.

In one embodiment, the adhesive layer comprises a substantially solid, coherent adhesive composition, as opposed to a liquid, gel, or dry particulate or powdery composition. As such, the adhesive layer advantageously comprises one or more coherent regions or masses of a substantially solid adhesive composition that do not readily run or flow. A substantially solid and coherent adhesive layer in combination with a gel better adheres to a person's teeth and does not readily diffuse into the surrounding oral cavity on its own, absent becoming diluted by saliva or moisture in a person's mouth, compared to a gel used by itself. This helps maintain the adhesive composition and bleaching gel between the optional barrier layer and a person's teeth being bleached and helps prevent diffusion of the bleaching agent into the surrounding oral cavity. This, in turn, promotes better tooth bleaching, patient compliance, and reduces the tendency of the user to taste the bleaching composition when in use.

The tooth adhesion agent within the adhesive layer contributes or provides increased adhesiveness to teeth when moistened with saliva or water. In one embodiment, the tooth adhesion agent advantageously remains substantially non-adhesive when the adhesive composition is in a dry or substantially solid condition but becomes adhesive to teeth when the adhesive composition is moistened with, e.g., water or saliva. A non-limiting example of a suitable tooth adhesion agent is polyvinyl pyrrolidone (PVP), although it is within the scope of the invention to use other tooth adhesion agents known in the art.

The adhesive composition, as well as intermediate compositions used to make the substantially solid adhesive composition, may include other components as desired to yield a final composition having desired properties. These include both inert components and active agents. Examples of inert components include, but are not limited to, plasticizers and humectants (e.g., glycerin, sorbitol, and polyethylene glycol), volatile solvents (e.g., water and alcohols), stabilizing agents (e.g. BEDTA), neutralizing agents, thickening agents (e.g., fumed silica), flavorants, sweeteners, and the like.

Examples of active agents include bleaching agents (e.g., hydrogen peroxide or solid complexes or analogues of hydrogen- peroxide, such as carbamide peroxide or sodium fluoride or other fluoride salts), antimicrobial agents (e.g., chlorhexidine), antiplaque agents, anti-tartar agents, or other medicaments.

In one embodiment, the dental bleaching gel comprises a dental bleaching agent and a tackifying agent, typically dispersed within a liquid carrier or vehicle. Exemplary dental bleaching agents include aqueous hydrogen peroxide, carbamide peroxide, sodium perborate, sodium percarbonate, and the like. It is, of course, within the scope of the invention to use any dental bleaching agent known in the art.

Exemplary tackifying agents include PVP, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like. It is, of course, within the scope of the invention to use any tackifying agent known in the art.

Exemplary liquid carriers or vehicles include water, alcohols, polyols (e.g., glycerin, sorbitol, polyethylene glycol, propylene glycol, and polypropylene glycol), and the like.

According to one embodiment, the substantially solid adhesive composition is made by first forming a flowable liquid or gel adhesive composition intermediate that is subsequently dried to form a substantially solid adhesive layer. This may be performed by heating or otherwise causing one or more volatile solvents to be driven off by evaporation, thus leaving behind a substantially solid adhesive composition or layer. The drying process may be performed before or after the adhesive composition intermediate is placed into contact with a barrier layer. The adhesive intermediate composition can be molded or shaped into a desired tray-like configuration. Alternatively, the adhesive intermediate composition can be cast onto a forming surface and dried to form a substantially solid sheet that is molded, stamped or otherwise formed into a desired shape. Thereafter, a dental bleaching gel is attached or applied to an inner surface of the adhesive layer and a barrier layer is optionally applied or attached to an outer surface of the adhesive layer. The dental bleaching gel can be applied to the adhesive layer before or after the barrier layer, or in the absence of a barrier layer.

According to one embodiment, the adhesive layer can be formed by spreading a flowable adhesive composition intermediate onto the surface of a large or continuous polymeric sheet followed by heating, such as in a forced air oven or desiccation device, to drive off a substantial portion of the water or other solvent that was used to form the adhesive composition intermediate in order to yield a substantially solid adhesive layer. Thereafter, individual intermediate tray-like devices can be molded or stamped from the large or continuous polymeric sheet coated with the substantially solid adhesive composition or layer and then separated as individual devices. Alternatively, a solid sheet comprising the adhesive composition or layer can be separated from the polymer sheet and molded, stamped or otherwise formed into a desired shape. Once the intermediate tray-like devices or adhesive layers have been formed, the dental bleaching gel may be applied or placed adjacent to an inner surface of the adhesive layer.

An advantage of providing a bleaching gel that is separate from the adhesive layer, rather than a bleaching agent that is contained within the adhesive layer, is that it provides a bleaching composition or device that is more stable or consistent relative to the amount of active bleaching agent. Heating the adhesive composition intermediate to drive off the water so as to yield a substantially solid adhesive composition can destabilize a bleaching agent contained therein and cause it to become less potent. Because the dental bleaching gel is generally not heated during manufacture of bleaching composition and devices according to the invention, greater stability and potency of the bleaching agent can be achieved.

In yet another embodiment, a dental tray can be coated with a flowable adhesive composition intermediate, such as by painting or spreading, which is then heated or allowed to dry at room temperature to form the substantially solid adhesive composition. The dental bleaching gel may then be applied to the inside surface of the adhesive layer.

The size and shape of dental bleaching compositions and devices according to the invention can be tailored to more readily fit a person's upper or lower dental arch. They may also be tailored to fit persons having differently-sized or shaped dental arches. The dental bleaching compositions and devices are advantageously designed so as to substantially cover the front and lingual surfaces of the teeth to be bleached. Bleaching both surfaces yields more esthetically appealing teeth. Moreover, bleaching both the front and lingual surfaces helps in bleaching the interproximal spaces between adjacent teeth. The dental bleaching compositions and devices are advantageously flexible and adhesive so as to readily conform to a wide variety of differently-sized teeth and dental arches.

The dental bleaching compositions and devices according to the invention are preferably in the shape of a dental tray having a front side wall, a rear side wall, and a trough between the front and rear side walls. Having the shape of a dental tray facilitates placement of the dental bleaching composition or device over a person's teeth by minimizing the amount of manipulation that is necessary to obtain a good fit between the composition or device and the person's teeth. Dental bleaching compositions or devices that are in the shape of a dental tray are easier to install over a person's teeth compared to flat bleaching strips or patches. In addition, the inventive dental bleaching compositions and devices are designed to more reliably remain in place over the person's teeth compared to conventional bleaching strips. The result is more effective tooth bleaching and better patient compliance.

According to one embodiment, the dental bleaching composition or device has a horseshoe shape and a U-shaped trough like a conventional bleaching tray. In another embodiment, the bleaching composition or device has an L-shaped profile or "trough". It will be appreciated, however, that dental bleaching compositions and devices according to the invention can have any longitudinal profile or shape (e.g., they can be straight or have any desired degree of longitudinal curvature from one end of the composition or device to the other). The trough may have any desired cross-sectional shape (e.g., the trough can be V-shaped, trapezoidal, rectangular, or other geometric shape).

To facilitate the ability of a dental bleaching composition or device to conform to the various shapes and sizes among dental arches, the dental bleaching composition or device may include mechanical features such as a notch within the front side wall, preferably within an edge near the center of the front side wall, and/or a notch within the rear side wall, preferably within an edge near the center of the rear side wall. Notches allow the tray-like bleaching composition or device to more easily conform to differently-sized dental arches. In this way, the dental bleaching composition or device can be designed so as to be "one-size fits all."

The dental bleaching compositions and devices according to the invention can be designed to be worn for any desired time period. Increasing the concentration of dental bleaching agent within the dental bleaching gel generally reduces the required bleaching time. Nevertheless, due to the extremely comfortable fit and reliable adhesion between the inventive dental bleaching compositions and devices and the person's teeth, it is possible to wear such compositions and devices for extended periods of time in order to ensure even and thorough bleaching. Dental bleaching compositions and devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive bleaching devices such as large, bulky bleaching dental appliances.

The dental bleaching compositions or devices can be designed to be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours. Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

For convenience of use, multiple dental bleaching compositions or devices may be packaged together and sold as a kit. In one embodiment, the number of dental bleaching compositions or devices provided with each kit can equal the number of sessions that represent a prescribed bleaching regimen. To efficiently utilize the space within a kit package, multiple dental bleaching compositions or devices can be stacked and interested together. The dental bleaching compositions or devices can be sealed collectively or individually as desired. They may contain a removable protective layer on their interior surfaces to protect the adhesive layer and the dental bleaching gel from contamination or moisture, both of which can possibly cause premature decomposition of a peroxide bleaching agent.

It is within the scope of the invention to provide barrier layers, adhesive layers, and a dental bleaching gel that are initially separate and that are brought together by the end user. The adhesive composition of the adhesive layer may be a dry or substantially solid insert or it may be a liquid or gel that is applied to a barrier layer and allowed to dry prior to placement of the dental bleaching gel adjacent to the adhesive layer and placement of the finished dental bleaching device over the person's teeth.

These and other advantages and& features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introductions and Definitions

Figure 1:
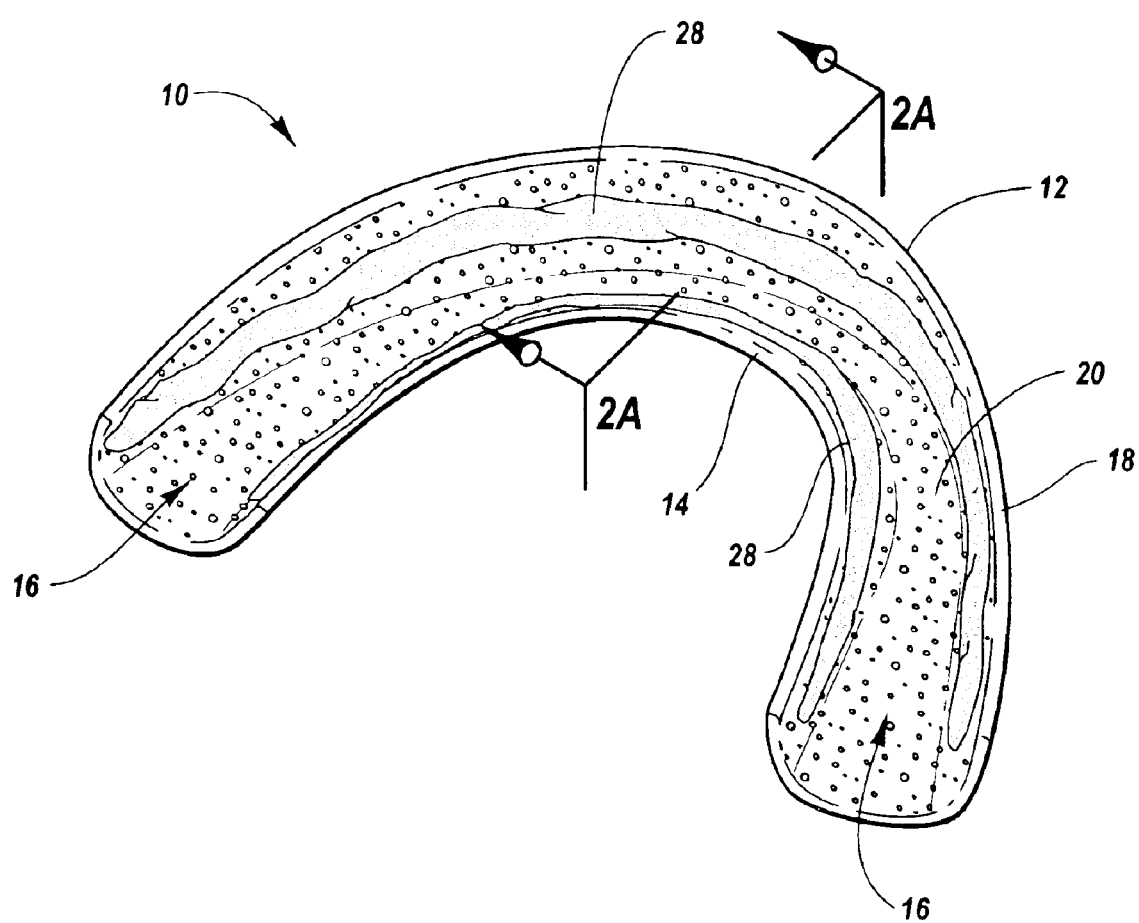
FIG. 1 is a perspective view of an exemplary dental bleaching device according to the invention in the shape of a dental tray comprising a barrier layer, an adhesive layer, and a dental bleaching gel.

The present invention generally relates to improved dental bleaching compositions and devices used to bleach a person's teeth. The inventive bleaching compositions include an adhesive layer that becomes more adhesive to teeth when moistened with water or saliva and a dental bleaching gel adjacent to the adhesive layer. The inventive dental bleaching devices include a moisture-resistant barrier layer, an adhesive layer that becomes more adhesive to teeth when moistened with water or saliva, and a dental bleaching gel adjacent to the adhesive layer. When the bleaching composition or device is placed over a person's teeth, the adhesive layer reliably adheres to the teeth, allowing the dental bleaching gel to remain in contact with the teeth to be bleached. The optional barrier layer protects the adhesive layer and dental bleaching gel from diffusing away from the person's teeth as a result of ambient saliva or moisture found within the person's mouth.

The inventive bleaching compositions and devices are more adhesive to teeth than conventional dental bleaching strips. Such compositions and devices are also less intrusive than bulky, over-the-counter, non-custom or boil-and-bite dental trays. In some ways they are as reliable, or even more reliable than, custom-fitted dental trays in maintaining a dental bleaching gel against a person's teeth. In some cases, they are also as comfortable, or even more comfortable, than custom-fitted trays.

The term "barrier layer", as used herein, refers to one or more layers of a moisture-resistant material that protects the adhesive layer and bleaching gel from ambient moisture and saliva found within a person's mouth when the dental bleaching device is placed over the person's teeth. The barrier layer may also serve to protect the adhesive layer and bleaching gel from moisture or other contaminants during storage and prior to use. The barrier layer may be in any desired form including, but not limited to, a sheet laminated to a surface of the adhesive layer, a coating applied to a pre-formed adhesive layer or bleaching composition, or a dental treatment tray.

The term "adhesive layer", as used herein, refers to one or more regions of an adhesive composition that has been formulated or processed so as to be substantially solid, coherent, and non-flowable. The adhesive layer may comprise a single continuous region or layer adjacent to the bleaching gel and, optionally, a barrier layer, or it may comprise a plurality of discontinuous regions or layers adjacent to a barrier layer and spaced-apart by random or predetermined intervals.

The term "substantially solid", as used herein, refers to an adhesive composition or layer that is in a solid or semi-solid condition. In one aspect, a "substantially solid" adhesive composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of an adhesive composition or layer, also excludes dry particulate adhesive compositions or powders because dry particulates and powders readily flow when subjected to gravity and/or are readily separated (i.e., the particles as a whole have little or no internal cohesion). Moreover, powders or particulates, when viewed as a whole, are not coherent or solid.

One characteristic of the "substantially solid" adhesive compositions or layers is that they become more adhesive when an exposed surface thereof is moistened with, e.g., saliva or water. When moistened, the surface of the adhesive composition or layer turns into a sticky material that is able to more strongly adhere to teeth compared to a substantially solid adhesive composition or layer that has not been moistened. The adhesive composition at the surface may become a viscous liquid, paste or gel, at least temporarily, depending on the amount of moisture that is applied to the surface of the "substantially solid" adhesive composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" adhesive composition or layer over time (e.g., during a bleaching procedure in which the adhesive layer or composition is protected from saliva and ambient moisture in a person's mouth by a moisture-resistant barrier layer).

The term "bleaching gel", as used herein, refers to a dental bleaching composition that has been formulated or processed so as to be flowable (e.g., it can be expressed out of a syringe orifice or other dispensing means known in the art). The bleaching gels according to the invention are, however, preferably sufficiently thick or viscous that they will not run out of a dental tray or tray-like device into which the bleaching gel is placed. In one embodiment, they are rubbery or highly viscous so as to e more suitable for use in a prefilled tray. When a bleaching gel is placed next to a dry adhesive layer, the two dissimilar compositions may tend to reach an equilibrium wherein some of the moisture or other liquid carrier of the bleaching gel diffuses into the adhesive layer, thus further increasing the viscosity and stiffness of the bleaching gel. The bleaching gel may comprise a single continuous bead or layer adjacent to the adhesive layer, or it may comprise a plurality of discontinuous regions or layers spaced-apart by random or predetermined intervals.

The term "dental tray", as used herein, refers to any composition or device having a tray-like shape so as to facilitate placement of the composition or device over at least a portion of a person's dental arch. A "dental tray" or "tray-like" composition or device includes a front side wall configured to engage front surfaces of a person's teeth when in use, a rear side wall extending laterally from the front side wall, either abruptly by one or more distinct angles or non-abruptly by a curved transition portion, configured to engage lingual surfaces of the person's teeth, and a trough between said front and rear side walls. A "dental tray" may be configured so that a portion of the front side wall, rear side wall, or a transition portion thereof (e.g., a bottom wall), engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°. In practice, the front and rear side walls will be offset by an angle that is preferably less than about 150°, more preferably less than about 120°, and most preferably less than about 90°.

In the case where the front and rear side walls are connected by a transition portion (e.g., a trough having a U-shaped or rectangular cross section), at least a portion of the front and rear side walls may be substantially parallel (i.e., be offset by an angle of approximately 0°) or offset by a very small angle. In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls may be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when referring to a dental tray or treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The terms "shaped bleaching composition", "shaped bleaching device" and "shaped adhesive composition", as used herein, refer to a composition that has been formulated or processed so that at least a portion of the composition is substantially solid, coherent, and non-flowable. The "shape" of the adhesive layer, bleaching composition, or bleaching device is primarily determined by. the shape and relative rigidity of the barrier layer and/or adhesive layer. The bleaching gel typically does not determine or contribute to the "shape" of the bleaching compositions and devices but conforms to the shape of the adhesive layer and/or barrier layer.

The term "molecular weight", as used herein, shall refer to number average molecular weight expressed in Dalton, unless otherwise specified.

II. Dental Bleaching Compositions and Devices

The dental bleaching compositions according to the invention can exist alone or in combination with a barrier layer as part of a dental bleaching device. Dental bleaching compositions according to the invention include an adhesive layer that becomes more adhesive to teeth when moistened by, e.g., saliva or water, and a dental bleaching gel adjacent to an inner surface of the adhesive layer. A moisture-resistant barrier layer adjacent to an outer surface of the adhesive layer protects the adhesive layer and bleaching gel from ambient moisture within a person's mouth during use. Following are preferred examples of barrier layers, adhesive layers, and bleaching gels according to the invention, as well as characteristics of bleaching compositions or devices made therefrom.

A. Barrier Layers

According to one embodiment of the invention, the barrier layer comprises a thin, flexible membrane formed from a moisture-resistant polymer material. In a preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Such materials may be provided in the form of large, flat, flexible sheets to which an adhesive composition or layer is applied. Alternatively, such sheets may be applied or attached to an existing adhesive composition or a bleaching composition comprising a substantially solid adhesive layer and a bleaching gel.

Notwithstanding the foregoing, it is within the scope of the invention to provide barrier layers having any desired material, thickness or rigidity so long as the barrier layer provides at least some moisture protection relative to the adhesive composition or layer and bleaching gel. The barrier layer may comprise a conventional dental tray, examples of which include both customized and non-custom dental trays. The barrier layer may be as simple as a layer of a moisture resistant material that is sprayed or painted on, applied by dipping, or otherwise applied to an existing shaped adhesive or bleaching composition (e.g., one that is in the form of a dental tray or that otherwise has a desired shape).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. Plasticizers, flow additives, and fillers known in the art can be used as desired to modify the properties of any of the foregoing polymers used to form the barrier layer.

As will be discussed below, some solid adhesive compositions are more adhesive to polymer materials comprising the barrier layer than others, often depending on the tooth adhesion agent that is used. It has been found that, as between polyethylene, paraffin and polyethylene terephthalate, substantially solid adhesive compositions tend to adhere more strongly to polyethylene terephthalate, particularly MYLAR.

It is also within the scope of the invention to utilize barrier layers that are formed onto a surface of a previously formed adhesive layer or bleaching composition, such as by adhering a sheet or tray-like barrier layer to the adhesive layer or bleaching composition. Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose, butyl cellulose, t-butyl cellulose, and the like.

B. Adhesive Layers

Prior to being moistened in preparation for or during use, adhesive layers within dental bleaching compositions and devices according to the invention preferably comprise a substantially solid and coherent adhesive composition, as opposed to a liquid, a flowable gel, or a dry powder or particulate. The adhesive layer may comprise a single coherent mass or region, or it may comprise a plurality of coherent masses or regions of a substantially solid adhesive composition. Providing a substantially solid and coherent adhesive layer better maintains the dental bleaching gel against the teeth being bleached instead of diffusing into the surrounding oral cavity, as compared to bleaching gels that are loaded without an adhesive layer into customized or non-customized dental trays or that are applied using bleaching strips. This, in turn, promotes better tooth whitening and patient compliance by reducing irritation to surrounding oral tissues and/or at least some of the bad taste normally associated with dental bleaching.

Substantially solid adhesive compositions that comprise the adhesive layer include at least one tooth adhesion agent and, optionally, one or more inert component or active agents. In the case where an active agent is included, it may be advantageously dispersed within a substantially solid matrix comprising the tooth adhesion agent. Following are preferred tooth adhesion agents, as well as exemplary insert components and active agents that may optionally be included within the adhesive composition.

1. Tooth Adhesion Agents

The tooth adhesion agent may comprise any known tackifying agent that is substantially non-adhesive, or less adhesive, when the adhesive composition or layer is substantially solid but which becomes more adhesive to teeth when the adhesive composition or layer is moistened with, e.g., water or saliva. A presently preferred tooth adhesion agent is polyvinyl pyrrolidone (PVP). PVP polymers have been found to provide excellent adhesion to polymer barrier layers made from PE, PET, polyurethane, and paraffin, to be substantially non-adhesive when the adhesive composition is dry to the touch, and to have superior adhesion to teeth when a surface of a substantially solid adhesive composition is moistened with saliva or water.

Non-limiting examples of polyvinyl pyrrolidone polymers that have been used in formulating adhesive compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid adhesive compositions or layers according to the invention.

Other tooth adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tooth adhesion agent, it has been found that a polyethylene oxide polymer having a molecular weight of 1 million provides better adhesion to barrier layers such as MYLAR than a polyethylene oxide polymer having a molecular weight of 100,000.

The one or more tooth adhesion agents are preferably included in an amount in a range of about 10% to about 90% by weight of the substantially solid adhesive composition (exclusive of any bound water or other solvent), more preferably in a range of about 20% to about 80% by weight of the substantially solid adhesive composition, and most preferably in a range of about 40% to about 75% by weight of the substantially solid adhesive composition.

2. Inert Components

The adhesive compositions and layers may include inert components in addition to the tooth adhesion agent, as desired, to yield a final composition or layer having desired properties. Examples of "inert" components include, but are not limited to, plasticizers and humectants (e.g., glycerin, sorbitol, polyethylene glycol, propylene glycol, and polypropylene glycol), volatile solvents (e.g., water and alcohols, such as ethanol), stabilizing agents (e.g., EDTA and citric acid), neutralizing agents.(e.g., sodium hydroxide), thickening agents (e.g., fumed silica), flavorants, sweeteners, and the like.

When water is used as a solvent when manufacturing adhesive compositions or layers according to the invention and then driven off by evaporation to yield a substantially solid dental bleaching or desensitizing composition, it is postulated that a significant amount of water remains bound or associated with the hydrophilic components within the adhesive composition, including the tooth adhesion agent, any inert components (e.g., polyols added as humectants, stabilizing agents, neutralizing agents, and/or thickening agents), and any hydrophilic active agents (e.g., bleaching and/or desensitizing agents). Although the amount of residual water has not yet been determined, it is believed that approximately 10% of the water added initially remains after the initially flowable adhesive composition intermediate has been dried sufficiently to yield the substantially solid adhesive composition or layer.

3. Active Agents

A wide variety of active agents known in the dental and oral arts can be included within the adhesive composition or layer. Examples of include bleaching agents (e.g., hydrogen peroxide or solid complexes or analogues of hydrogen peroxide, such as carbamide peroxide or sodium perborate), desensitizing agents (e.g., potassium nitrate), remineralizing agents (e.g., sodium fluoride or other fluoride salts), antimicrobial agents (e.g., chlorhexidine), antiplaque agents, anti-tartar agents, or other medicaments.

Examples of substantially solid adhesive compositions and layers that include one or more active agents are disclosed in U.S. application Ser. No. 10/446,235, filed May 27, 2003; U.S. application Ser. No. 10/446,471, filed May 27; 2003; U.S. application Ser. No. 10/637,237, filed Aug. 8, 2003; U.S. application Ser. No. 10/646,484, filed Aug. 22, 2003; and U.S. application Ser. No. 10/646,443, filed Aug. 22, 2003. For purposes of disclosing solid adhesive compositions and layers that include one or more active agents, the foregoing applications are incorporated herein by reference.

When one or more bleaching agents are included within the substantially solid adhesive composition, they are preferably included in an amount in a range of about 5% to about 80% by weight of the substantially solid adhesive composition, more preferably in a range of about 10% to about 60% by weight of the substantially solid adhesive composition, and most preferably in a range of about 20% to about 50% by weight of the substantially solid adhesive composition.

When potassium nitrate is included within the substantially solid adhesive composition as a desensitizing agent, it is preferably included in an amount in a range of about 0.01% to about 50% by weight of the substantially solid adhesive composition, more preferably in a range of about 0.1% to about 25% by weight of the substantially solid adhesive composition, and most preferably in a range of about 0.5% to about 10% by weight of the substantially solid adhesive composition.

When included in combination with a dental bleaching agent, potassium nitrate is preferably included in an amount in a range of about 0.01% to about 2% by weight of the substantially solid adhesive composition, more preferably in a range of about 0.05% to about 1% by weight of the substantially solid adhesive composition, and most preferably in an amount of about 0.5% by weight of the substantially solid adhesive composition. It has been found that including potassium nitrate in these amounts creates a synergistic effect with the dental bleaching agent that appears to enhance tooth whitening. It also provides the highest level of tooth desensitization when used with a bleaching agent.

For treating periodontal disease, chlorhexidine gluconate is a preferred medicament and is preferably included in an amount in a range of about 0.01 to about 50% by weight of the substantially solid adhesive composition, more preferably in a range of about 0.05% to about 25% by weight of the substantially solid adhesive composition, and most preferably in a range of about 0.1% to about 10% by weight of the substantially solid adhesive composition. Other antibacterial agents or medicaments may be included in the same concentration ranges.

C. Bleaching Gels

The bleaching compositions and devices according to the invention may include any bleaching gel known in the art. The bleaching gel may comprise a solid layer positioned so as to cover a person's front tooth surfaces, rear tooth surfaces, or both, or it may comprise separate beads, layers or islands of gel separated by a space. Preferred bleaching gels are those that are substantially viscous and tacky in order to assist the adhesive layer in retaining the bleaching composition or device against a person's teeth during use. In one aspect of the invention, the bleaching gels according to the invention may comprise at least one bleaching agent and any of the adhesive composition intermediates used to manufacture the substantially solid adhesive compositions or layers described herein.

Exemplary dental bleaching gels, and methods for making such gels, which may be used to manufacture the bleaching compositions and devices according to the invention are disclosed in U.S. Pat. Nos. 5,376,006; 5,785,527; 5,851,512; 5,858,332; 5,985,249; 6,306,370; 6,309,625; 6,312,671; 6,322,774; 6,368,576; 6,387,353; 6,500,408; and 6,503,485. For purposes of disclosing dental bleaching gels, and methods of making such gels, the foregoing patents are incorporated herein by reference.

In general, the dental bleaching gels will include at least one dental bleaching agent, at least one tackifying agent, and a liquid or gel carrier or vehicle into which the dental bleaching agent and tackifying agent are dispersed. The bleaching gel may optionally include other active agents (e.g., desensitizing agents, remineralizing agents, antimicrobial agents, and the like). An advantage of providing a bleaching gel separate from the adhesive layer is that it provides a bleaching composition or device that is more stable or consistent relative to the amount of active bleaching agent. Heating an adhesive composition intermediate to drive off the water so as to yield a substantially solid adhesive composition can destabilize a bleaching agent contained therein and render it less potent. Because the dental bleaching gel is generally not heated during manufacture of bleaching composition and devices according to the invention, greater stability and potency of the bleaching agent may be achieved. Following are preferred bleaching agents, tackifying agents, and carriers or vehicles.

1. Bleaching Agents

A common dental bleaching agent that is known to bleach teeth and that has been found to be safe for oral use is hydrogen peroxide. However, hydrogen peroxide does not itself exist free in nature, but only as an aqueous solution or as a complex. Aqueous hydrogen peroxide is an acceptable dental bleaching agent to the extent that an anhydrous bleaching gel is not desired. Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within the dental bleaching gels according to the invention can have any desired concentration, e.g., between 1–90% by weight of the dental bleaching gel. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

The one or more bleaching agents are preferably included in an amount in a range of about 1% to about 60% by weight of the dental bleaching gel, more preferably in a range of about 3% to about 40% by weight of the dental bleaching gel, and most preferably in a range of about 5% to about 30% by weight of the dental bleaching gel.

2. Tackifying Agents

Useful tackifying agents that may be used in the bleaching gel include any of the tooth adhesion agents disclosed herein for use in manufacturing the substantially adhesive compositions or layers according to the invention. The main difference between a "tackifying agent" within a "bleaching gel", and a "tooth adhesion agent" within an "adhesive composition" or "adhesive layer" is the physical state. On the one hand, a tackifying agent within a bleaching gel is already mixed with a liquid or gel carrier or vehicle such that the resulting dental bleaching gel is immediately sticky and tacky to the touch as a result of the tackifying agent. On the other hand, an adhesive composition or layer typically becomes much more adhesive to teeth when the adhesive composition or layer is moistened by saliva or water as a result of the tooth adhesion agent. The adhesive composition or layer may initially be non-adhesive and dry to the touch prior to moistening with saliva or water.

One useful tackifying agent is polyvinyl pyrrolidone (PVP). Non-limiting examples of polyvinyl pyrrolidone polymers that have been used in formulating dental bleaching gels according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

Other useful tackifying agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

The one or more tackifying agents are preferably included in an amount in a range of about 1% to about 50% by weight of the dental bleaching gel, more preferably in a range of about 3% to about 30% by weight of the dental bleaching gel, and most preferably in a range of about 5% to about 20% by weight of the dental bleaching gel.

3. Carriers and Vehicles

The dental bleaching gel will typically include one or more liquid or gel carriers or vehicles into which the dental bleaching agent, tackifying agent, and other components are dispersed. Examples of liquid or gel carriers or vehicles include, but are not limited to, water, alcohols (e.g., ethyl alcohol), and polyols (e.g., glycerin, sorbitol, polyethylene glycol, polyethylene oxide, propylene glycol, and polypropylene glycol). The carrier or vehicle will typically comprise the balance of components in the dental bleaching gel in addition to the bleaching agent, tackifying agent, and any other components.

4. Other Components

The dental bleaching gels according to the invention may optionally include other components as desired to yield a bleaching gel having desired properties. Examples include stabilizing agents (e.g., EDTA), neutralizing agents (e.g., sodium hydroxide), thickening agents (e.g., fumed silica), desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

D. Characteristics of Dental Bleaching Compositions and Devices

The dental bleaching compositions and devices according to the invention are preferably in the shape of a dental tray having a front side wall, a rear side wall, and a trough between the front and rear side walls. Having the shape of a dental tray facilitates placement of the dental bleaching composition or device over a person's teeth by reducing the amount of manipulation that is necessary to obtain a good fit between the composition or device and the person's teeth.

Dental bleaching compositions or devices that are in the shape of a dental tray or that have a tray-like configuration, and that have a substantially solid adhesive layer that becomes more adhesive when moistened with water or saliva, are easier to install over a person's teeth compared to bleaching strips or patches, which are initially flat and which must be manipulated so as to wrap the initially flat strip or patch around the occlusal or incisal edges of the teeth in order to cover the front and lingual tooth surfaces. In addition, the inventive dental bleaching compositions or devices are designed to more reliably adhere and remain in place over the person's teeth compared to conventional bleaching strips, which employ a dental bleaching gel immediately adjacent to a flimsy backing layer. The result is more effective tooth bleaching and better patient compliance. In contrast to conventional bleaching strips, which are not recommended for use while a person eats, drinks, smokes or sleeps, dental bleaching compositions and devices according to the invention can be designed so as to be worn while talking, sleeping, eating, drinking, smiling, frowning, grimacing, yawning, coughing, smoking; or making virtually any facial expression or mouth contortion.

Figure 2A:
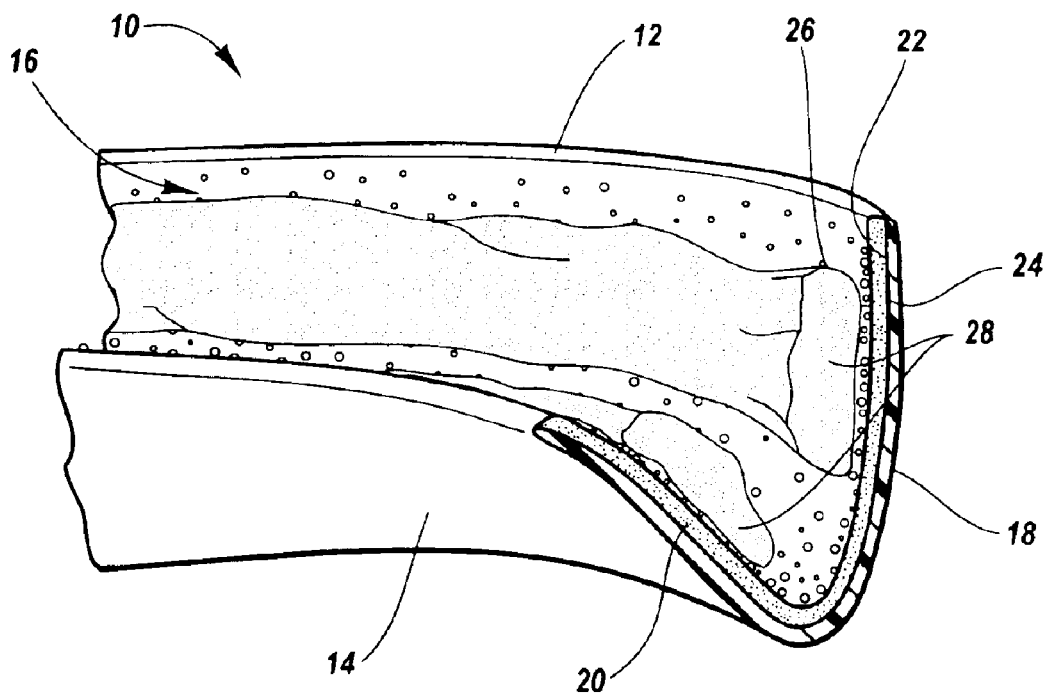
FIG. 2A is a cross-sectional view of the dental bleaching device depicted in FIG. 1.

According to one currently preferred embodiment, the dental bleaching compositions and devices have a horseshoe shaped longitudinal profile and a trough with a U-shaped cross section, much like a conventional bleaching tray. An exemplary dental bleaching device is depicted in FIGS. 1 and 2A. FIG. 1 is a perspective view of a dental bleaching device 10 having a front side wall 12 and a rear side wall 14 that together have a generally horseshoe shape in a longitudinal dimension and that define a trough 16 having a generally U-shaped cross section. The U-shaped cross section of the trough is seen more clearly in FIG. 2A.

The dental bleaching device 10 further includes a barrier layer 18, preferably comprising a moisture-resistant material, an adhesive layer 20, preferably comprising a substantially solid adhesive composition, and a dental bleaching gel 28. As best seen in FIG. 2A, the adhesive layer 20 includes an outer surface 22, which is adjacent to an interior surface 24 of the barrier layer 18, and an inner surface 26, which is adjacent to the dental bleaching gel. In one embodiment, both the dental bleaching gel and a portion of the inner surface 26 of the adhesive layer 20 are designed to directly contact a person's teeth when the dental bleaching device 10 is in use. An upper edge of the front side wall 12 can be designed so as to terminate at or shy of the gingival margin of a person's dental arch when the dental bleaching device 10 is in use.

Figure 2B:
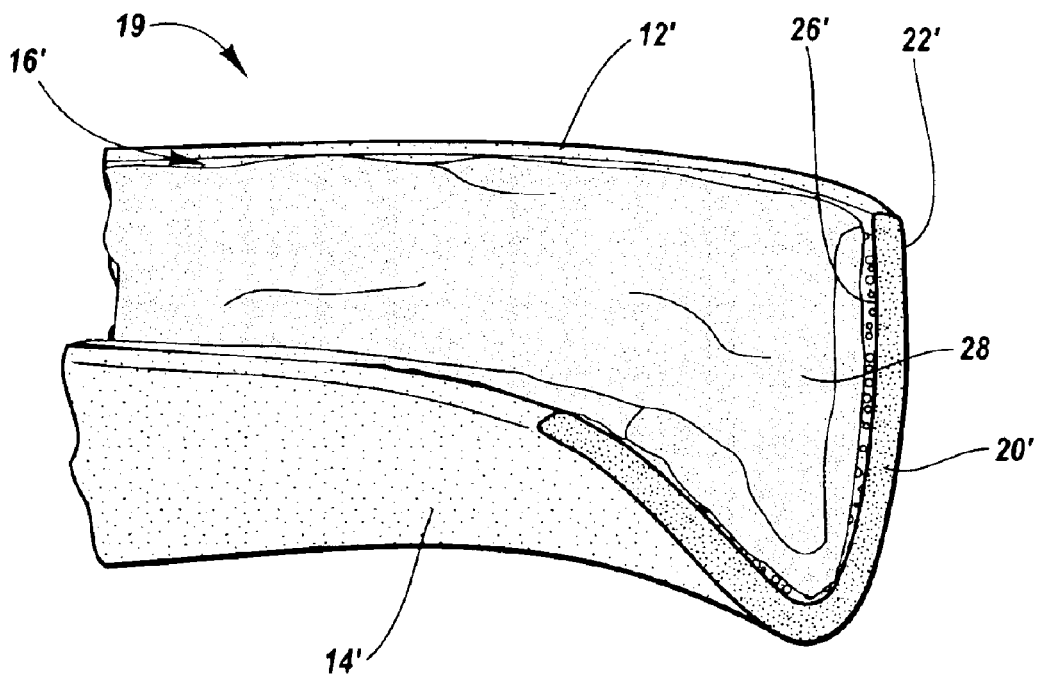
FIG. 2B is a cross-sectional view of en exemplary dental bleaching composition according to the invention in the shape of a dental tray, but without a barrier layer.

FIG. 2B alternatively depicts a dental bleaching composition 19 comprising an adhesive layer 20' in the shape of a dental tray, so as to have a front side wall 12' and a rear side wall 14', and a dental bleaching gel 28 adjacent to an inner surface 26' of the adhesive layer 20'. The dental bleaching composition 19 differs from the dental bleaching device 20 of FIGS. 1 and 2A because it includes no barrier layer. The adhesive layer 20' also includes an exterior surface 22' that may optionally be coated with a water-resistant barrier layer or material if desired (see FIG. 2A) to protect the dental bleaching composition (more particularly the adhesive layer 20' and dental bleaching gel 28) from saliva or ambient moisture (see FIG. 2A). The dental bleaching composition 19 may be sold alone or together with a moisture-resistant barrier layer, or a material used to make a barrier, that can be placed adjacent to the exterior surface 22' of the adhesive layer 20' prior to or during use.

Figure 3:
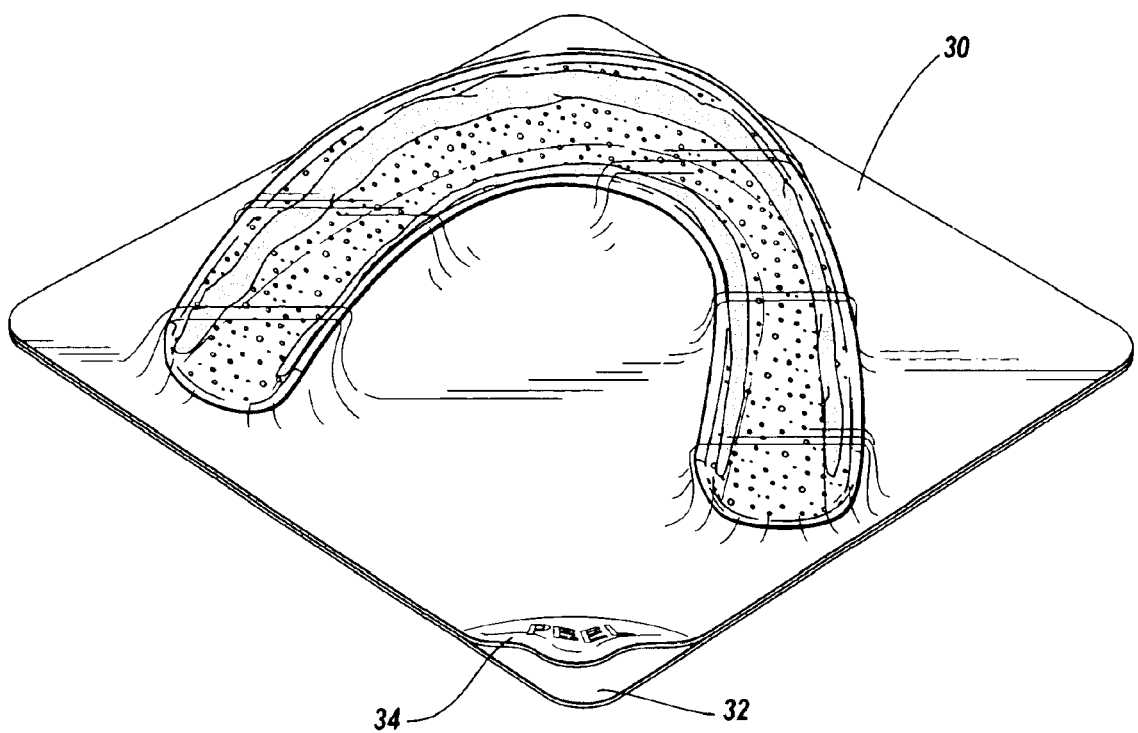
FIG. 3 illustrates a dental bleaching composition or device according to the invention contained within a sealed protective package having a peelable cover.

In order to protect dental bleaching compositions or devices according to the invention from contaminants during storage and prior to use, the bleaching compositions or devices can be packaged within a sealed container or package. As illustrated in FIG. 3, the bleaching device 10 (or bleaching composition 19) can be sealed within a protective package 30 that includes a rigid support layer 32 and a peelable cover 34. When it is desired to use the bleaching device 10 (or bleaching composition 19), the peelable cover 34 is removed and the bleaching device 10 (or bleaching composition 19) is removed or separated from the support layer 32. In addition to, or instead of, the protective package 30, the bleaching device 10 (or bleaching composition 19) may alternatively include a removable protective layer (not shown) that is temporarily placed within the trough adjacent to the dental bleaching gel 28. When it is desired to use the bleaching device 10 (or bleaching composition 19), the removable protective layer is removed so as to expose the bleaching gel.

Figure 4:
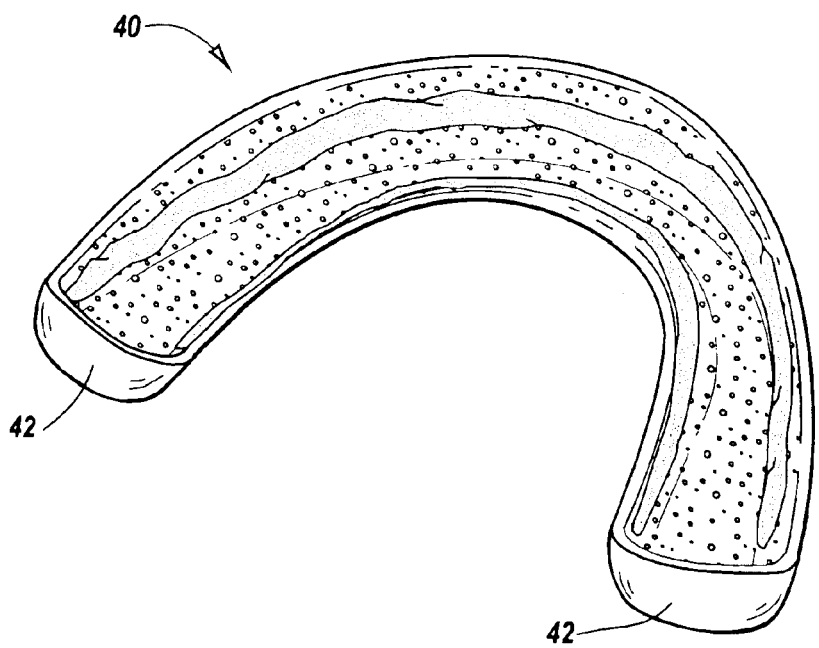
FIG. 4 is a perspective view of an exemplary dental bleaching composition or device that is similar to the bleaching device depicted in FIG. 1, or the bleaching composition of FIG. 2B, but that further includes a terminal side wall on each longitudinal

FIG. 4 illustrates a dental bleaching composition or device 40 that is a variation of the U-shaped dental bleaching device 10 of FIGS. 1 and 2A or the dental bleaching composition 19 of FIG. 2B. The main difference is that each longitudinal end 42 of the dental bleaching composition or device 40 is raised so as to at least partially enclose the last tooth on each side of a person's dental arch when the bleaching composition or device 40 is in use.

Figure 5:
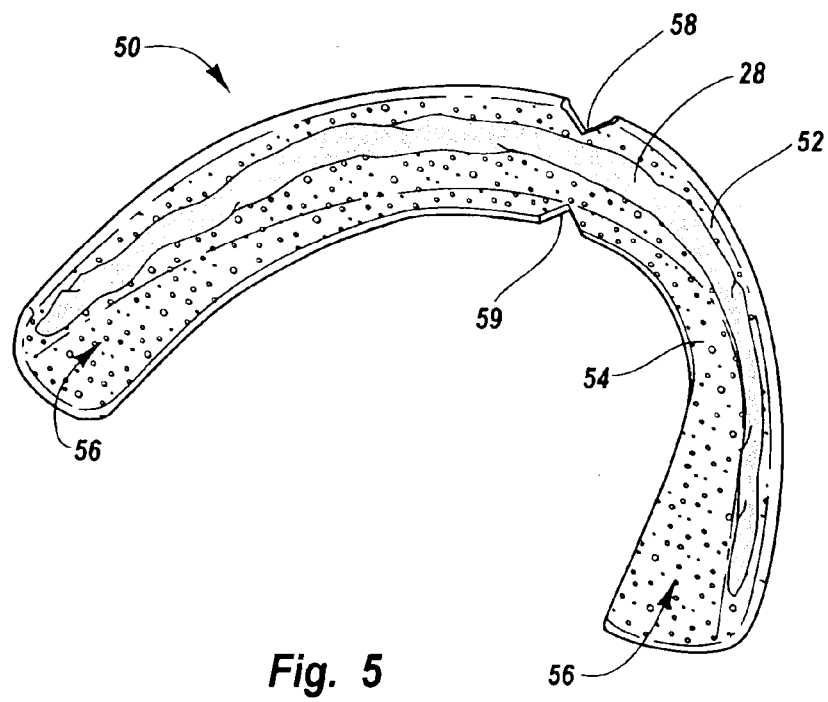
FIG. 5 is a perspective view of an exemplary dental bleaching composition or device having an L-shaped trough and a curved longitudinal profile.

FIG. 5 illustrates an alternative embodiment of a dental bleaching composition or device 50 according to the invention that has an L-shaped cross section. More particularly, the dental bleaching composition or device 50 includes a front side wall 52 and a rear side wall 54 extending laterally from the front side wall 52 so as to form a trough 56 having an approximate L-shaped cross section. The L-shaped bleaching composition or device 50 of FIG. 5 is somewhat easier to initially place over a person's dental arch compared to the U-shaped bleaching composition or devices of FIGS. 1–4. This is due to the approximately planar orientation of the rear side wall 54 relative to the occlusal or incisal edges of a person's teeth when the front side wall 52 of the dental bleaching composition or device 50 is initially placed and adhered against the front surfaces of a person's teeth. On the other hand, more manipulation of the L-shaped bleaching composition or device 50 is generally required to form and adhere the rear side wall 54 against the lingual surfaces of the person's teeth as a result of the greater initial offset angle between the front side wall 52 and rear side wall 54. However, the ability of dental bleaching compositions or devices according to the invention to adhere to tooth surfaces immediately after placement over a person's teeth, and even more so after initial wetting of the adhesive layer, facilitates the process of conforming the front side wall 52 and rear side wall 54 to the person's tooth surfaces.

In the case of the dental bleaching composition or device 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped bleaching composition or device is folded back against the lingual tooth surfaces during use, it can be readily seen that a bleaching composition or device having an L-shaped trough is merely a variation of a composition or device having a V-shaped trough. Thus, for purposes of this disclosure and the appended claims, the side wall 54 shall constitute, and fall within the definition of, a "rear side wall".

To facilitate the ability of a dental bleaching composition or device to conform to the varying shapes and sizes among dental arches, the dental bleaching composition or device may include mechanical features such as one or more notches within the front or rear side walls. As shown in FIG. 5, the dental bleaching composition or device 50 includes a notch 58 in an outer edge near the center of the front side wall 52 and a notch 59 in an outer edge near the center of the rear side wall 54. Notches 58 and 59 allow the tray-like bleaching composition or device to more easily spread open or compress when being conformed to differently-sized dental arches. In this way, the dental bleaching composition or device 50 can more easily be a "one-size fits all" composition or device.

Figure 6:
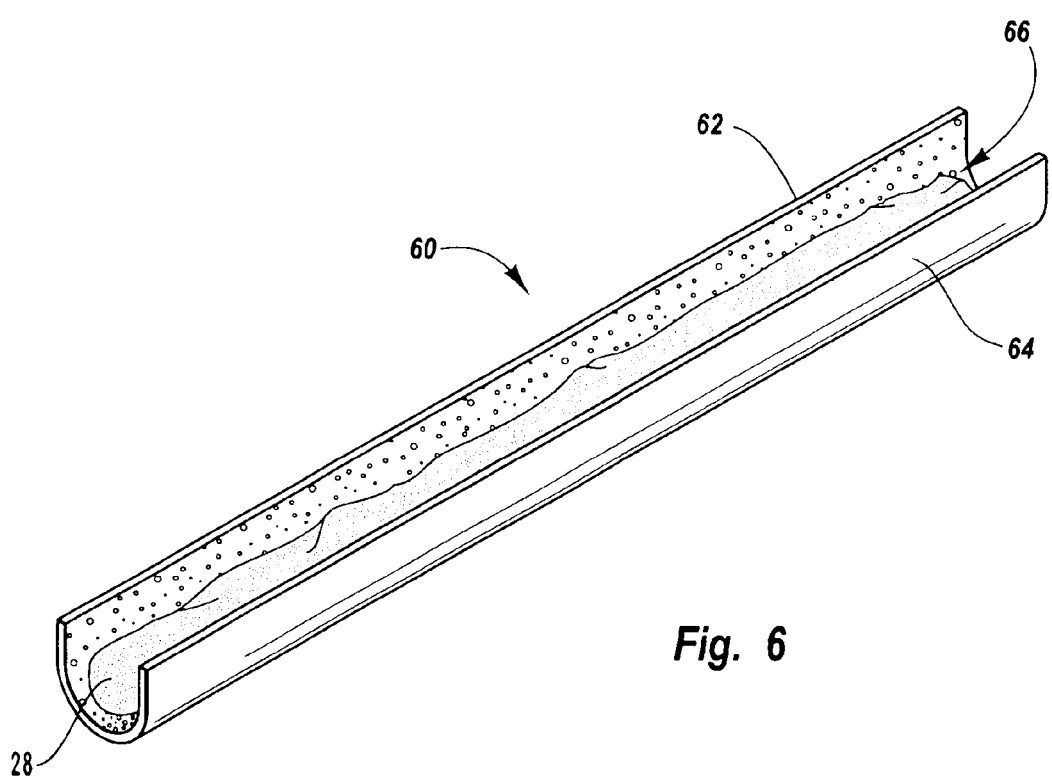
FIG. 6 is a perspective view of an exemplary dental bleaching composition or device having a U-shaped trough and a substantially straight longitudinal profile.

FIG. 6 depicts an alternative embodiment of a dental bleaching composition or device 60 according to the invention, which includes a front side wall 62 and a rear side wall 64 that define a U-shaped trough 66. Instead of being horseshoe shaped like the dental bleaching composition or device of FIGS. 1–5, or otherwise having a curved longitudinal profile, the dental bleaching composition or device 60 of FIG. 6 has a substantially straight or linear longitudinal profile.

Figure 7:
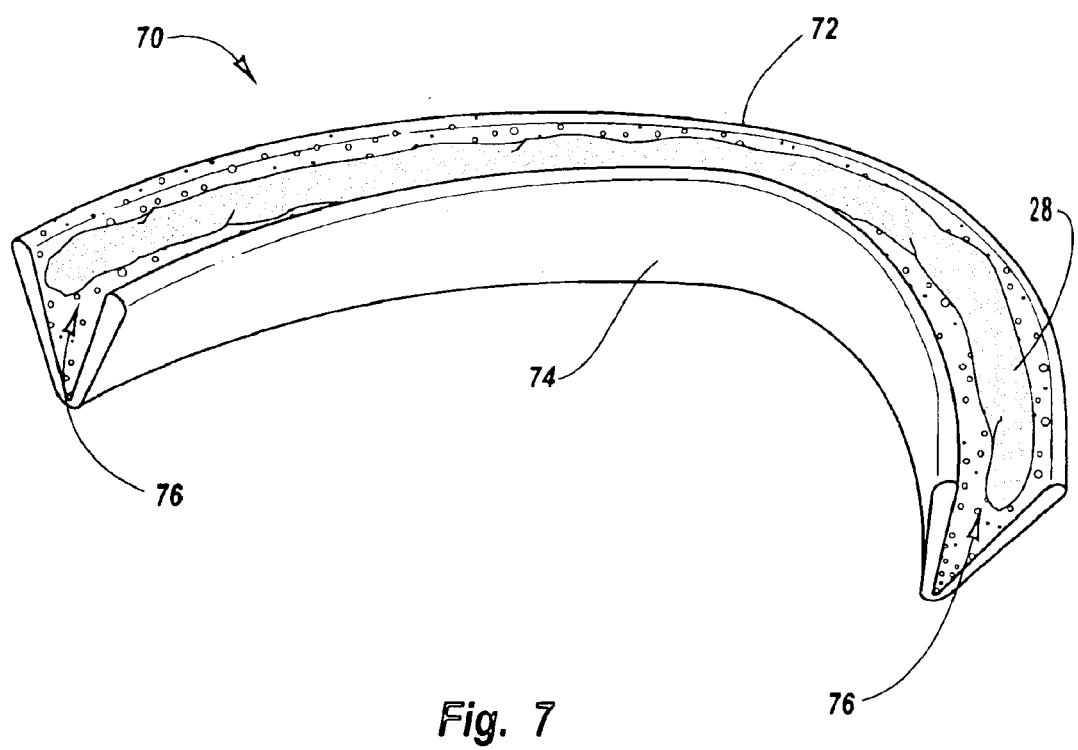
FIG. 7 is a perspective view of an exemplary dental bleaching composition or device having a V-shaped trough and a curved longitudinal profile.

FIG. 7 depicts yet another alternative embodiment of a dental bleaching composition or device 70 according to the invention. The dental bleaching composition or device 70 includes a front side wall 72 and a rear side wall 74 that define a V-shaped trough 76 and a curved longitudinal profile. The main-difference between the V-shaped bleaching composition or device 70 of FIG. 7 and the L-shaped bleaching composition or device 50 of FIG. 5 is the angle at which the front and rear side walls are laterally offset from each other.

Notwithstanding the foregoing examples, it will be appreciated that dental bleaching compositions and devices according to the invention can have any longitudinal shape (e.g., they can have a straight or curved longitudinal profile from one end to the other). The front and rear side walls may define a trough of any desired cross-sectional shape (e.g., the trough can be trapezoidal, rectangular, or any other desired geometric shape).

The size and shape of dental bleaching compositions and devices according to the invention can be tailored to more readily fit either a person's upper dental arch or lower dental arch. They can be sized so as to bleach all or merely a subset of a person's teeth. The dental bleaching compositions and devices may be sufficiently adhesive and flexible so as to readily conform to a wide variety of differently-sized teeth and dental arches. The dental bleaching compositions and devices are advantageously designed so as to substantially cover the front and lingual surfaces of the teeth to bleached. Bleaching both surfaces yields more esthetically appealing teeth, although it is certainly within the scope of the invention to bleach more of one surface than another. Bleaching the front and lingual surfaces helps to bleach the interproximal spaces between a person's teeth. If left unbleached, stained interproximal spaces can form a dark ring or silhouette around each tooth.

In general, the thickness of the barrier layer and/or the adhesive layer can be selected to yield a dental bleaching device having a desired strength and flexibility. In order for the barrier layer to remain flexible so as to conform to a person's teeth, the barrier layer will generally have a thickness ranging from about 0.025 mm to about 1.5 mm, preferably in a range of about 0.05 to about 1 mm. The adhesive layer will generally have a thickness ranging from about 0.1 mm to about 3 mm. The thickness of the adhesive layer can also be selected depending on the intended duration of each bleaching session. In generally, increasing the thickness of the adhesive layer will provide a longer adhesion of the dental bleaching device or composition to a person's teeth. By way of example, for short wear times, the adhesive layer will preferably have a thickness ranging from about 0.1 mm to about 0.5 mm. For intermediate wear times, the adhesive layer will preferably have a thickness ranging from about 0.5 mm to about 2 mm. For professional use and for overnight bleaching, the adhesive layer will preferably have a thickness ranging from about 2 mm to about 3 mm.

The amount of dental bleaching gel within the trough of the dental bleaching composition or device can be selected to yield a dental bleaching composition or device having a desired tackiness and/or bleaching potency. In the case where the adhesive layer includes no bleaching agent, the dental bleaching gel will be required to provide the sum total of the bleaching agent. In such cases, the thickness of the dental bleaching gel may be increased, all things being equal. By contrast, in the case where the adhesive layer also includes a bleaching agent, the dental bleaching gel will not be required to provide the entirety of the bleaching agent. In such cases, the thickness of the dental bleaching gel may be decreased, all things being equal.

In addition, the more viscous and tacky the dental bleaching gel, the less deleterious will be the bleaching gel on the overall ability of the bleaching composition or device to adhere to a person's teeth. In such cases, the cross-sectional thickness of the dental bleaching gel may be increased, all things being equal. By contrast, the less viscous and tacky the dental bleaching gel, the more deleterious will be the bleaching gel on the overall ability of the bleaching composition or device to adhere to a person's teeth. In such cases, the cross-sectional thickness of the dental bleaching gel may be advantageously decreased, all things being equal.

III. Methods of Making Dental Bleaching Compositions Bleaching Devices Incorporation such Compositions The various components that make up the inventive dental bleaching compositions and devices according to the invention can be assembled or brought together in any desired order. According to one embodiment, a shaped adhesive composition or layer is first made by forming a flowable adhesive composition intermediate that is then shaped and dried to form a substantially solid adhesive composition or layer in the form of a dental tray or tray-like device. This may be performed by heating or otherwise causing one or more volatile solvents to be driven off by evaporation, thus leaving behind the substantially solid adhesive layer. Thereafter, a bleaching gel is placed against an inner surface of the adhesive layer.

An optional barrier layer may also be placed against an outer surface of the adhesive layer in order to protect the adhesive layer and bleaching gel from ambient moisture within a person's mouth. The barrier layer may be placed against the adhesive layer either before or after the adhesive composition is dried so as to become substantially solidified. In one embodiment, the barrier layer may comprise a pre-formed dental tray. In another, it may comprise a thin, flexible sheet. In yet another embodiment, the barrier layer may initially comprise a flowable barrier material or precursor that is later cured or hardened, such as by removing a solvent by evaporation, by chemical or light curing, or by cooling a thermoplastic melt.

In an alternative embodiment, the adhesive intermediate composition can be cast onto a forming surface and dried to form a substantially solid sheet, which is subsequently molded, stamped or otherwise formed into a desired shape. Thereafter, a dental bleaching gel is attached or applied to an inner surface of the adhesive layer, and a barrier layer is optionally applied or attached to an outer surface of the adhesive layer. The dental bleaching gel can be applied to the adhesive layer before or after the barrier layer, or in the absence of a barrier layer.

According to another embodiment, the adhesive layer can be made by spreading a flowable adhesive composition intermediate onto the surface of a large or continuous polymeric sheet (e.g., using a screeding device). The polymeric sheet and adhesive composition intermediate are then placed into a forced air oven or other appropriate desiccation device in order to heat and drive off a substantial portion of the water or other solvent used to form the flowable adhesive composition intermediate. Removal of the volatile solvent yields an adhesive layer comprising a substantially solid adhesive composition. Thereafter, individual intermediate tray-like devices can be molded or stamped from the large or continuous polymeric sheet coated with the substantially solid adhesive composition or layer and then separated as individual devices. Alternatively, a solid sheet comprising the adhesive composition or layer can be separated from the polymer sheet and molded, stamped or otherwise formed into a desired shape. Once the intermediate tray-like devices or adhesive layers have been formed, the dental bleaching gel may be applied or placed adjacent to an inner surface of the adhesive layer.

In yet another embodiment of the invention, a barrier layer in the form of a dental tray or tray-like device (e.g., a customized or non-custom tray) can be coated with a flowable adhesive composition intermediate. The adhesive composition intermediate is then heated together with the dental tray or otherwise allowed to dry in order to form an adhesive layer comprising a substantially solid adhesive composition. Thereafter, a dental bleaching gel is applied to an inner surface of the adhesive layer in order to yield a finished dental bleaching device according to the invention. Any or all of these assembly processes can be performed during commercial manufacture of the bleaching device, or by an end user as part of using a bleaching kit.

IV. Methods of Using Dental Bleaching Compositions and Bleaching Devices Incorporating such Compositions The dental bleaching compositions and devices according to the invention can be designed to be worn for any desired time period. Increasing the concentration of dental bleaching agent generally reduces the time required to effect bleaching. Nevertheless, due to the extremely comfortable fit and reliable adhesion between the inventive dental bleaching compositions or devices and the person's teeth, it is possible to wear such compositions or devices for extended periods of time in order to ensure more uniform bleaching. They may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

The dental bleaching compositions or devices according to the invention may be worn over a person's upper dental arch, lower dental arch, or both simultaneously. The ability to reliably and comfortably wear dental bleaching compositions or devices over the upper and lower dental arches simultaneously is another departure from bleaching strips, which are not recommended for use in bleaching the upper and lower dental arches at the same time.

Figure 8:
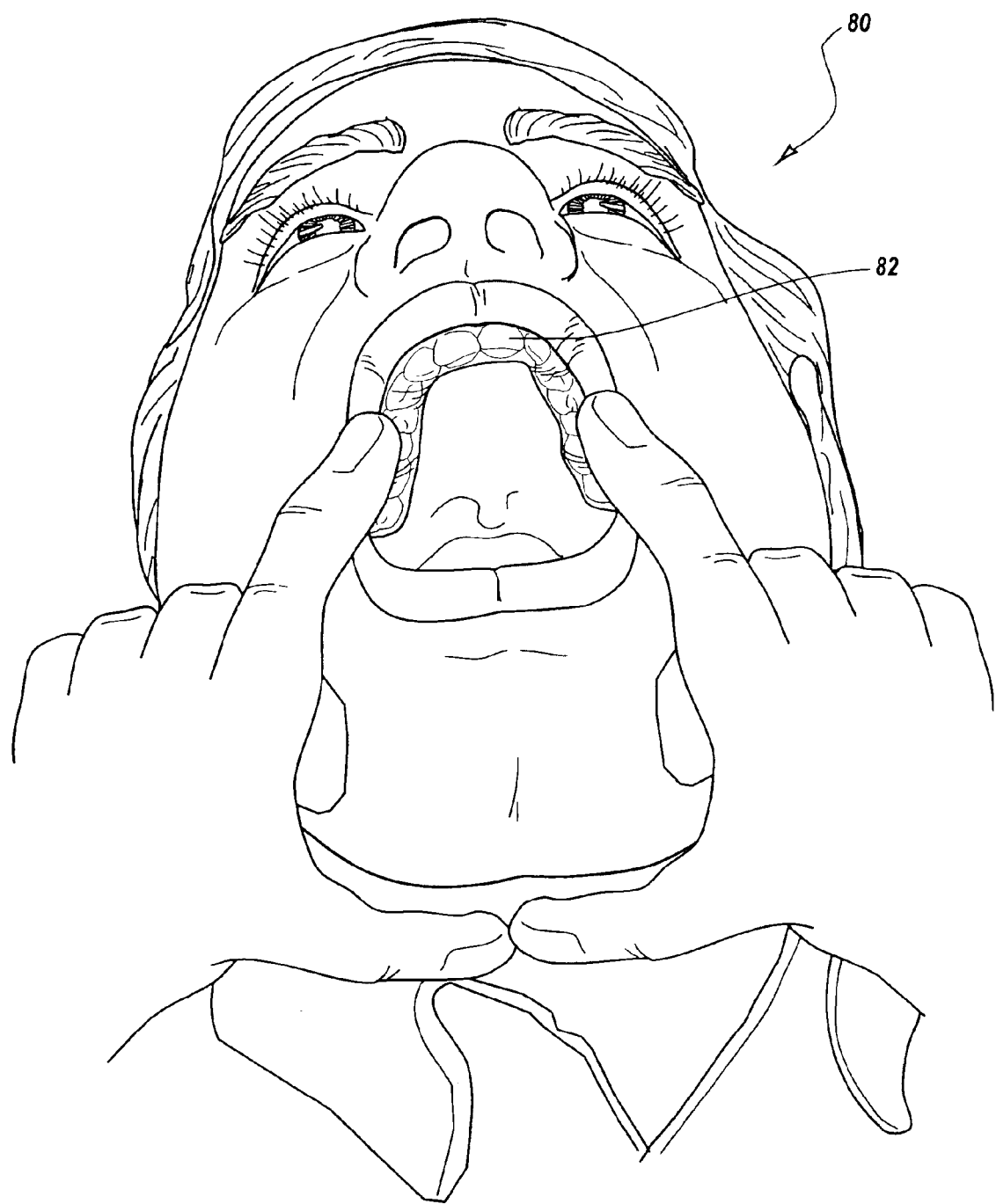
FIG. 8 illustrates a person placing a dental bleaching composition or device according to one embodiment of the invention over the upper dental arch.
Figure 9:
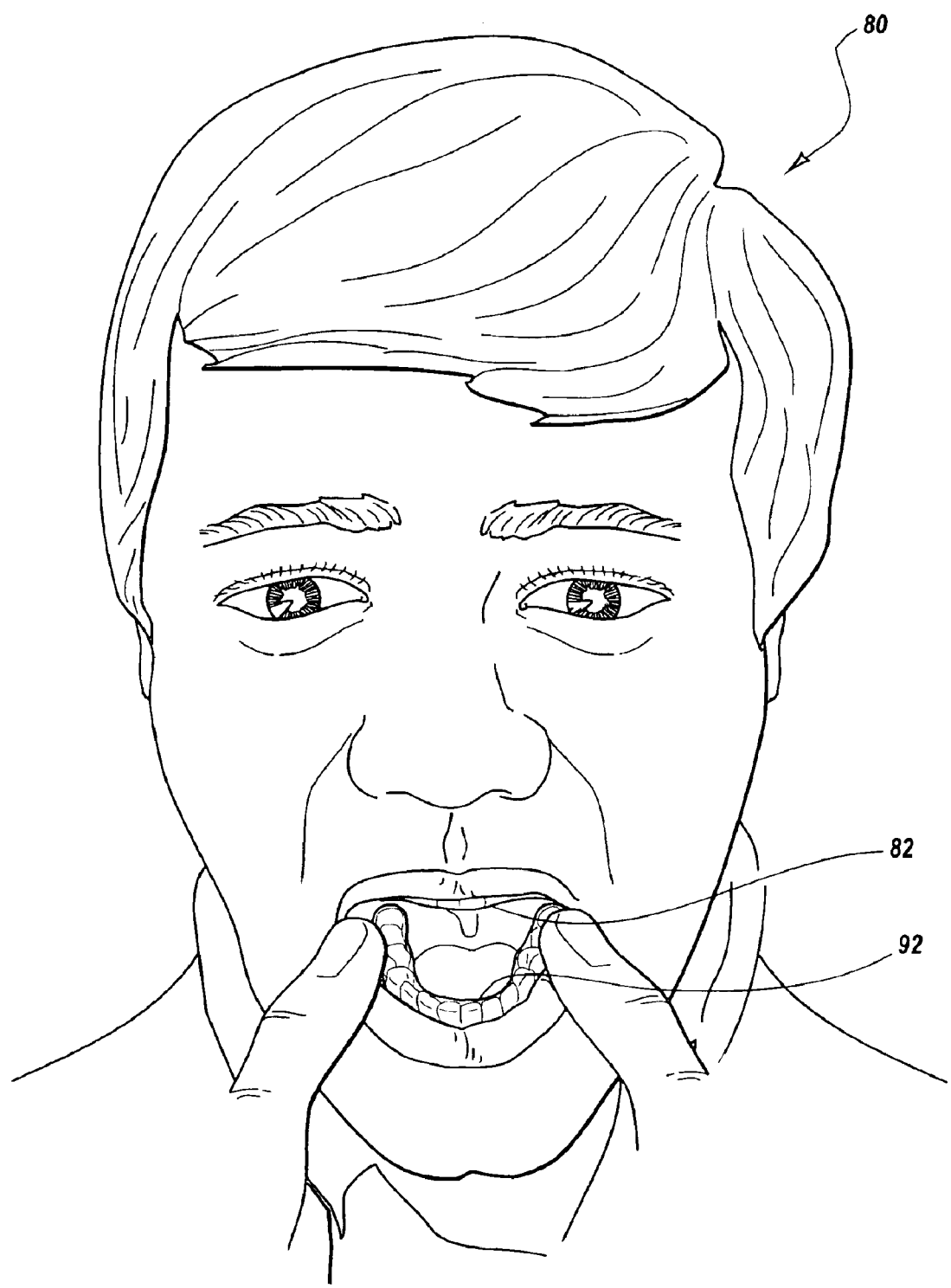
FIG. 9 illustrates a person placing a dental bleaching composition or device according to one embodiment of the invention over the lower dental arch, with a dental bleaching composition or device already placed over the upper dental arch.

FIG. 8 illustrates a person 80 placing a dental treatment composition or device 82 over the person's upper dental arch. FIG. 9 illustrates the person 80 placing a dental treatment composition or device 92 over the person's lower dental arch after having placed the dental treatment composition or device 82 over the upper dental arch. It will be appreciated, however, that the dental treatment compositions or devices can be placed over a person's upper and lower dental arches in any desired order.

To remove the dental bleaching composition or device, a user can pry open a corner of the barrier layer and/or adhesive layer using a fingernail or rigid tool and then pull the remainder off. Any residual adhesive composition and/or bleaching gel that remains adhered to the person's teeth can be removed by washing or flushing water over the person's teeth, and/or by brushing. Although the inventive dental bleaching compositions are very adhesive to teeth when protected from excessive moisture, they can be formulated to quickly break down and dissolve when flushed with excess water and/or by gentle mechanical action (e.g., brushing).

The dental bleaching compositions or devices can be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions according to the invention may be repeated as many times as needed to obtain a desired degree of tooth bleaching. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Bleaching Kits

For convenience of use, multiple dental bleaching compositions or devices may be packaged together and sold as a kit. In the case of dental bleaching compositions that do not initially include a barrier layer, a separate barrier layer, or material used to form a barrier layer, may be optionally included within the kit. In one embodiment, the number of dental bleaching compositions or devices provided with each kit may equal the number of sessions that represent a prescribed bleaching regimen. Because of the ease of placing the inventive dental bleaching compositions or devices over a person's teeth, coupled with the reliability with which they adhere to teeth, the likelihood that a particular bleaching compositions or device will fail, or otherwise not work as intended, is greatly diminished compared to conventional bleaching strips.

To efficiently utilize the space within a kit package, multiple dental bleaching compositions or devices can be stacked or interested together. The dental bleaching compositions or devices can be sealed collectively or individually as desired. A protective package 30 is depicted in FIG. 3. The bleaching compositions or devices may optionally contain a removable protective layer on an interior surface to protect the bleaching gel from contamination or moisture.

It is within the scope of the invention to provide barrier layers and bleaching composition that are initially separate and that are brought together by the end user. For example, the bleaching composition may comprise a pre-shaped insert in the shape of a horse-shoe that is placed into a trough of a tray-like barrier layer, with or without actually adhering the adhesive layer to the barrier layer. Alternatively, a flowable adhesion composition intermediate can be placed within the trough of a dental tray or tray-like barrier layer and allowed to dry prior to placement of the dental bleaching gel against an inner surface of the substantially solid adhesive layer. Thereafter, a bleaching gel is placed adjacent to an inner surface of the substantially solid adhesive layer. A bleaching gel may also be placed by a user adjacent to an inner surface of a shaped adhesive layer or composition in the absence of a barrier layer, or prior to placing a barrier layer adjacent to an outer surface of the adhesive layer.

VI. Examples of the Preferred Embodiments

The following are several examples of dental bleaching compositions and devices that have been formulated and manufactured according to the invention. The exemplary formulations and manufacturing conditions are given by way of example, and not by limitation, in order to illustrate dental bleaching compositions and devices that have been found to be useful for bleaching a person's teeth. Unless otherwise indicated, all percentages are by weight.

Examples 1–21 are directed to the manufacture of adhesive dental bleaching layers that become more adhesive when moistened by saliva or water. Examples 22–26 are directed to the manufacture of adhesive dental desensitizing layers that become more adhesive when moistened by saliva or water. The adhesive bleaching and desensitizing layers of Examples 1–26 therefore comprise exemplary adhesive compositions or layers according to the invention. Accordingly, exemplary dental bleaching compositions or devices according to the invention can be manufactured by placing any dental bleaching gel disclosed herein, or known in the art, adjacent to an inner surface of the bleaching or desensitizing layers of Examples 1–26.

Examples 27–32 are directed to the manufacture of adhesive compositions or layers that do not include any active agent. Exemplary dental bleaching compositions or devices according to the invention can be manufactured by placing any dental bleaching gel disclosed herein, or known in the art, adjacent to an inner surface of the adhesive layers of Examples 27–32.

Finally, Examples 33–37 are directed to exemplary dental bleaching gels that are suitable for use in manufacturing dental bleaching compositions or devices according to the invention. For example, dental bleaching compositions or devices according to the invention can be manufactured by placing the bleaching gels of Examples 33–37 adjacent to any of the adhesive layers described herein, including those formed according to Examples 1–32.

Example 1

An initially flowable intermediate composition suitable for use in manufacturing a substantially solid, cohesive, and non-flowable dental bleaching layer was formed by mixing together the following components:

| | |
|---|---|
| Carbamide Peroxide | 16% |
| Polyvinyl pyrrolidone (M.W. = 1.3 million) | 38% |
| Water | 46% |

The resulting intermediate composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The composition was spread using a spatula. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The dried bleaching layer adhered well to each of the polymer sheets. The coated sheets were placed back into the oven overnight to remove additional water.

The coated sheets were removed from the oven a second time, cut apart into smaller-sized pieces, and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch.

The tray-like devices were tested by placing them over a person's teeth. The residual saliva present on the tooth surfaces moistened the exposed surface of the bleaching layer and caused it to become sticky and very adhesive to teeth almost immediately. The tray-like devices were pressed against the teeth, which caused them to conform to the natural irregularities of the dental arch and adhere firmly against the teeth. This demonstrated that the bleaching layer formed in this example comprises an excellent adhesive layer.

A dental bleaching gel is placed within the trough of a tray-like device of this example, adjacent to an inner surface of the adhesive bleaching layer, to yield a tray-like dental bleaching device according to the invention. The dental bleaching gel is not heated prior to placing the dental bleaching device over a person's teeth, which helps preserves the potency and concentration of the dental bleaching agent within the bleaching gel compared to the carbamide peroxide contained within the adhesive bleaching layer.

The tray-like dental bleaching device is worn for varying time periods ranging from several minutes to several hours without becoming dislodged. The formation of oxygen bubbles within the bleaching gel indicates that the bleaching agent remains active. In some cases a noticeable bleaching effect is detected after just one bleaching session (e.g., a 2-hour bleaching session). Noticeable bleaching is typically detected after 1–3 bleaching sessions.

Example 2

An initially flowable intermediate composition suitable for use in manufacturing a substantially solid, cohesive, and non-flowable dental bleaching layer was formed by mixing together the following components:

| | |
|---|---|
| Carbamide Peroxide | 16% |
| PolyOx WSR 101 (M.W. = 1 million) | 7% |
| Water | 77% |

The resulting intermediate composition was spread over the surface of MYLAR sheets using a spatula. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. Unlike the bleaching layer of Example 1, the bleaching layer of Example 2 did not adhere strongly to the polymer sheets but was easily separated therefrom. The coated sheets were placed back into the oven overnight.

The coated sheets were removed from the oven a second time, cut apart into smaller-sized pieces, and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch.

The tray-like devices were tested by placing them over a person's teeth. The residual saliva present on the tooth surfaces moistened the exposed surface of the bleaching layer and caused it to become sticky and adhesive to teeth within a few seconds. The results of Example 2 indicate that, while polyethylene oxide was a satisfactory teeth adhesion agent, it was less satisfactory in promoting adhesion between a bleaching layer and a polymer sheet.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 3

An initially flowable intermediate composition suitable for use in manufacturing a substantially solid, cohesive, and non-flowable dental bleaching layer was formed by mixing together the following components:

| | |
|---|---|
| Carbamide Peroxide | 16% |
| Carbopol 974P | 5% |
| Aqueous NaOH (50%) | 6% |
| Water | 73% |

The resulting intermediate composition was spread over the surface of MYLAR sheets using a spatula. The coated sheets were heated in a forced air oven heated to a temperature of 50–70° C. for approximately 1 hour. The coated sheets were removed from the oven and inspected. Although the intermediate composition dried sufficiently to form a solid, it shrunk considerably, probably because of the large amount of water that was needed to cause Carbopol to form a gel. Shrinkage of the intermediate composition caused the polymer sheet to become partially shriveled up. Whereas shriveling of the polymer sheet was not desired, using carboxypolymethylene as a tooth adhesion agent resulted in a dried bleaching composition that adhered to a polymer sheet.

Thereafter, the coated sheets were removed from the oven after heating overnight, cut apart into smaller-sized pieces, and shaped into tray-like devices suitable for placement over a person's teeth. When placed over a person's teeth it took about 5 seconds for the bleaching layer to become moistened enough to start becoming sticky and adhesive to teeth. The tray-like device was able to conform to the person's teeth and remain in place after being pressed against the teeth for about 30–60 seconds.

The results of Example 3 indicate that, while Carbopol 974 P is able to adhere to a MYLAR sheet and appears to be a satisfactory tooth adhesion agent once the adhesive bleaching layer is sufficiently moistened, it presents a shrinkage problem that can cause undesirable deformation of thin, flexible polymer sheets. One would expect Carbopol 974 P to work better when used with less flexible sheets and/or preformed dental trays of sufficient rigidity to avoid shriveling or unwanted deformation.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 4

An initially flowable intermediate composition suitable for use in manufacturing a substantially solid, cohesive, and non-flowable dental bleaching layer was formed by mixing-together the following components:

| | |
|---|---|
| Polyethylene Oxide (M.W. = 100,000) | 20% |
| Glycerin | 2.5% |
| Sodium Percarbonate | 2.4% |
| Water | 75.1% |

The resulting intermediate composition was spread over the surface of MYLAR sheets as in Example 2. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer of Example 4 did not adhere at all to the MYLAR sheets. This indicates that the lower molecular weight polyethylene oxide of Example 4 was even less adhesive to MYLAR sheets than the higher molecular weight polyethylene oxide of Example 2. Sheets comprising an adhesive bleaching layer could also be formed by spreading the intermediate composition on a solid surface such as glass, drying the composition, and then peeling off the dried adhesive layer.

By comparison, when the intermediate composition of Example 1 was applied to a glass surface and then dried, it adhered so strongly that it could not readily be peeled off the glass surface. Instead, it had to be forcefully chipped or pried off using a razor blade.

The dried bleaching layer of Example 4 did, however, adhere to a person's teeth when moistened, although not as well as the bleaching layers of Examples 1–3. This indicates that the bleaching layer of Example 4 might have commercial application as an adhesive layer in a tray-like dental bleaching device to the extent that problems adhering to the barrier layer are overcome or are not an issue.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 5

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The resulting intermediate composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The intermediate composition had dried sufficiently so as to form a solid, coherent bleaching layer on the surface of the polymer sheets. Using a mixture of water and ethanol as the solvent allowed the intermediate composition to dry in less than time than the intermediate compositions of Examples 1–4. The inclusion of glycerin helped the bleaching layer remain more flexible and less brittle after drying. The bleaching layer adhered well to each of the polymer sheets. After initial drying, the coated sheets were placed back into the oven overnight.

The coated sheets were removed from the oven a second time, cut apart into smaller-sized pieces, and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 6

An initially flowable intermediate composition suitable for use in manufacturing a substantially solid, cohesive, and non-flowable dental bleaching layer was formed by mixing together the following components:

| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The resulting intermediate composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The intermediate composition had dried sufficiently so as to form a solid, coherent bleaching layer on the surface of the polymer sheets. The inclusion of polyethylene glycol helped the bleaching layer remain more flexible and less brittle after drying. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 7

An initially flowable intermediate composition suitable for use in manufacturing a substantially solid, cohesive, and non-flowable dental bleaching layer was formed by mixing together the following components:

| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. Using ethanol as the only solvent allowed the intermediate composition to dry in even less time than the compositions of Examples 5 and 6. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 8

An initially flowable intermediate composition suitable for use in manufacturing a substantially solid, cohesive, and non-flowable dental bleaching layer was formed by mixing together the following components:

| Carbamide Peroxide | 10% |
| Ethanol | 65% |
| Kollidon VA 90 F (M.W. = 1.3 million) | 20% |
| PEG 600 | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 9

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 10

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The resulting intermediate composition was spread over the surfaces of polyethylene, paraffin, and MYLAR sheets as described in Example 1. Aerosil 200 was added as a tackifying agent to promote adhesion of the intermediate composition to the polymer sheets. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 11

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 12

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The resulting intermediate composition was spread over the surface of MYLAR sheets as in Example 2. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer of Example 12 did not adhere well to the MYLAR sheets. It also shrunk somewhat after extended drying. The bleaching layer of Example 12 was able to adhere to a person's teeth when moistened.

A dental bleaching gel is placed within the trough of a tray-like composition formed from a bleaching layer of this example, adjacent to an inner surface of the adhesive bleaching layer, to yield a tray-like dental bleaching composition according to the invention. The dental bleaching device of this example is effective in bleaching teeth.

Example 13

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent of bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 14

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth:

Example 15

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 16

An initially flowable intermediate composition suitable for use in manufacturing a substantially solid, cohesive, and non-flowable dental bleaching layer was formed by mixing together the following components:

| | |
|---|---|
| Carbamide Peroxide | 15% |
| Polyvinyl pyrrolidone (M.W. = 1.3 million) | 32% |
| Water | 12.8% |
| Ethanol | 20% |
| Glycerin | 10% |
| Aerosil 200 | 5% |
| Calcium EDTA | 0.2% |
| Sodium Lauryl Sulfate | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 17

An initially flowable intermediate composition suitable for use in manufacturing a substantially solid, cohesive, and non-flowable dental bleaching layer was formed by mixing together the following components:

| | |
|---|---|
| Carbamide Peroxide | 15% |
| Polyvinyl pyrrolidone (M.W. = 1.3 million) | 26% |
| Water | 16.8% |
| Ethanol | 25% |
| Glycerin | 15% |
| Calcium EDTA | 0.2% |
| Sodium Lauryl Ether Sulfate | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 18

An initially flowable intermediate composition suitable for use in manufacturing a substantially solid, cohesive, and non-flowable dental bleaching layer was formed by mixing together the following components:

| | |
|---|---|
| Carbamide Peroxide | 15% |
| Polyvinyl pyrrolidone (M.W. = 1.3 million) | 32% |
| Water | 13.8% |
| Ethanol | 20% |
| Glycerin | 12% |
| Aerosil 200 | 5% |
| Calcium EDTA | 0.2% |
| Silwet L-7001 | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 19

An initially flowable intermediate composition suitable for use in manufacturing a substantially solid, cohesive, and non-flowable dental bleaching layer was formed by mixing together the following components:

| | |
|---|---|
| Calcium Peroxide | 20% |
| Carbamide Peroxide | 4% |
| Polyvinyl pyrrolidone (M.W. = 1.3 million) | 20% |
| Water | 11.8% |
| Ethanol | 20% |
| Glycerin | 18% |
| Aerosil 200 | 5% |
| Calcium EDTA | 0.2% |
| Sodium Lauryl Sulfate | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 20

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 (M.W. = 1.3 million) | 18.7% |
| Water | 42.3% |
| Ethanol | 13.3% |
| Glycerin | 12% |
| Aerosil 200 | 3.3% |
| Sodium Lauryl Sulfate | 0.33% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 21

An initially flowable intermediate composition suitable for use in manufacturing a substantially solid, cohesive, and non-flowable dental bleaching layer was formed by mixing together the following components:

| | |
|---|---|
| Carbamide Peroxide | 7.1% |
| Kollidon 90 (M.W. = 1.3 million) | 25% |
| Water | 10.7% |
| Ethanol | 50.7% |
| Glycerin | 2.9% |
| Aerosil 200 | 3.6% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. The dental bleaching device of this example is effective in bleaching teeth.

Example 22

An initially flowable intermediate composition suitable for use in manufacturing a substantially solid, cohesive, and non-flowable dental desensitizing layer was formed by mixing together the following components:

| | |
|---|---|
| Sodium Fluoride | 0.25% |
| Polyvinyl pyrrolidone (M.W. = 1.3 million) | 30% |
| Water | 69.75% |

The resulting intermediate composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness- of approximately 0.38 mm. The intermediate composition was spread using a screeding device. The coated sheets were heated in a forced air oven heated to a temperature of 50–70° C. for approximately 1 hour. The coated sheets were removed from the oven and inspected. The intermediate composition had dried sufficiently so as to form a solid, coherent desensitizing layer on the surface of the polymer sheets. The dried desensitizing composition adhered well to each of the polymer sheets.

The coated sheets were cut apart into smaller-sized pieces and shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch.

The tray-like devices were tested by placing them over a person's teeth. The residual saliva present on the tooth surfaces moistened the exposed surface of the desensitizing layer and caused it to become sticky and very adhesive to teeth almost immediately. The tray-like devices were pressed against the teeth, which caused them to conform to the natural irregularities of the dental arch and adhere firmly against the teeth. This demonstrated that the desensitizing layer formed in this example comprises an excellent adhesive layer.

A dental bleaching gel is placed within the trough of a tray-like device of this example, adjacent to an inner surface of the adhesive desensitizing layer, to yield a tray-like dental bleaching device according to the invention. The dental bleaching gel is not heated prior to placing the dental bleaching device over a person's teeth, which helps preserves the potency and concentration of the dental bleaching agent within the bleaching gel.

The tray-like dental bleaching device is worn for varying time periods ranging from several minutes to several hours without becoming dislodged. The formation of oxygen bubbles within the bleaching gel indicates that the bleaching agent remains active. In some cases a noticeable bleaching effect is detected after just one bleaching session (e.g., a 2-hour bleaching session). Noticeable bleaching is typically detected after 1–3 bleaching sessions.

Example 23

An initially flowable intermediate composition suitable for use in manufacturing a substantially solid, cohesive, and non-flowable dental desensitizing layer was formed by mixing together the following components:

| | |
|---|---|
| Sodium Citrate | 5% |
| Polyvinyl pyrrolidone (M.W. = 1.3 million) | 20% |
| Water | 75% |

The resulting intermediate composition was manufactured into tray-like devices according to the method described in Example 22. The desensitizing layer adhered well to the barrier layers comprising polymer sheets. The tray-like devices were tested by placing them over a person's teeth. The residual saliva present on the tooth surfaces moistened the exposed surface of the desensitizing layer and caused it to become sticky and very adhesive to teeth almost immediately. The tray-like devices were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. The dental bleaching device of this example is effective in bleaching teeth.

Example 24

An initially flowable intermediate composition suitable for use in manufacturing a substantially solid, cohesive, and non-flowable dental desensitizing layer was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The resulting intermediate composition was manufactured into tray-like devices according to the method described in Example 22. The desensitizing layer adhered well to the barrier layers comprising polymer sheets. The tray-like devices were tested by placing them over a person's teeth. The residual saliva present on the tooth surfaces moistened the exposed surface of the desensitizing layer and caused it to become sticky and very adhesive to teeth almost immediately. The tray-like devices were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. The dental bleaching device of this example is effective in bleaching teeth.

Example 25

An initially flowable intermediate composition suitable for use in manufacturing a substantially solid, cohesive, and non-flowable dental desensitizing layer was formed by mixing together the following components:

| | |
|---|---|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The resulting intermediate composition was manufactured into tray-like devices according to the method described in Example 22. The desensitizing layer adhered well to the barrier layers comprising polymer sheets. The tray-like devices were tested by placing them over a person's teeth. The residual saliva present on the tooth surfaces moistened the exposed surface of the desensitizing layer and caused it to become sticky and very adhesive to teeth almost immediately. The tray-like devices were pressed against the teeth, which caused them to conform to the natural irregularities of the dental arch and adhere firmly a against the teeth.

A dental bleaching gel is placed within the trough of a tray-like device of this example, adjacent to an inner surface of the adhesive desensitizing layer, to yield a tray-like dental bleaching device according to the invention. The dental bleaching device of this example is effective in bleaching teeth.

Example 26

An initially flowable intermediate composition suitable for use in manufacturing a substantially solid, cohesive, and non-flowable dental desensitizing layer was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The resulting intermediate composition was manufactured into tray-like devices according to the method described in Example 22. The desensitizing layer adhered well to the barrier layers comprising polymer sheets. The tray-like devices were tested by placing them over a person's teeth. The residual saliva present on the tooth surfaces moistened the exposed surface of the desensitizing layer and caused it to become sticky and very adhesive to teeth almost immediately. The tray-like devices were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. The dental bleaching device of this example is effective in bleaching teeth.

Example 27

An initially flowable adhesive composition intermediate suitable for use in manufacturing a substantially solid adhesive layer was formed by mixing together the following components:

| | |
|---|---|
| Water | 25% |
| Ethanol | 30% |
| Glycerin | 10% |
| Polyvinyl pyrrolidone (M.W. = 1.3 million) | 30% |
| Aerosil 200 | 5% |

The resulting adhesive composition intermediate was manufactured into tray-like compositions or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. The dental bleaching device of this example adheres well to teeth and is effective in bleaching teeth.

Example 28

An initially flowable adhesive composition intermediate suitable for use in manufacturing a substantially solid adhesive layer was formed by mixing together the following components:

| | |
|---|---|
| Water | 20% |
| Ethanol | 30% |
| Glycerin | 15% |
| Polyvinyl pyrrolidone (M.W. = 1.3 million) | 30% |
| Aerosil 200 | 5% |

The resulting adhesive composition intermediate was manufactured into tray-like compositions or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. The dental bleaching device of this example adheres well to teeth and is effective in bleaching teeth.

Example 29

An initially flowable adhesive composition intermediate suitable for use in manufacturing a substantially solid adhesive layer was formed by mixing together the following components:

| | |
|---|---|
| Water | 20% |
| Ethanol | 40% |
| Glycerin | 10% |
| Polyvinyl pyrrolidone (M.W. = 1.3 million) | 30% |

The resulting adhesive composition intermediate was manufactured into tray-like compositions or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. The dental bleaching device of this example adheres well to teeth and is effective in bleaching teeth.

Example 30

An initially flowable adhesive composition intermediate suitable for use in manufacturing a substantially solid adhesive layer was formed by mixing together the following components:

| | |
|---|---|
| Ethanol | 60.6% |
| Glycerin | 5.1% |
| Polyvinyl pyrrolidone (M.W. = 1.3 million) | 30% |
| Aerosil 200 | 4.3% |

The resulting adhesive composition intermediate was manufactured into tray-like compositions or intermediate devices according to the methods described in Examples 1 or 22. The adhesive layer adhered- well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. The dental bleaching device of this example adheres well to teeth and is effective in bleaching teeth.

Example 31

An initially flowable adhesive composition intermediate suitable for use in manufacturing a substantially solid adhesive layer was formed by mixing together the following components:

| | |
|---|---|
| Ethanol | 61.9% |
| Glycerin | 9.5% |
| Polyvinyl pyrrolidone (M.W. = 1.3 million) | 23.8% |
| Aerosil 200 | 4.8% |

The resulting adhesive composition intermediate was manufactured into tray-like compositions or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. The dental bleaching device of this example adheres well to teeth and is effective in bleaching teeth.

Example 32

An initially flowable adhesive composition intermediate suitable for use in manufacturing a substantially solid adhesive layer was formed by mixing together the following components:

| | |
|---|---|
| Ethanol | 63.6% |
| Glycerin | 9.1% |
| Polyvinyl pyrrolidone (M.W. = 1.3 million) | 27.3% |

The resulting adhesive composition intermediate was manufactured into tray-like compositions or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. The dental bleaching device of this example adheres well to teeth and is effective in bleaching teeth.

Example 33

A dental bleaching gel suitable for use in manufacturing dental bleaching compositions and devices according to the invention was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 ($SiO_2$) | 7% |
| Peach Flavor | 2% |
| Polyethylene Glycol (M.W. = 20,000) | 20% |

The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more). Like any dental tray filled with a conventional dental bleaching composition, the dental tray of this example was easily dislodged from the person's mouth. Moreover, the bleaching gel was easily expressed out of the dental tray and into the person's oral cavity by normal mouth movements, such as talking, yawning or clenching of teeth.

Thereafter, the dental bleaching gel was used to form dental bleaching devices according to the invention by being placed adjacent to one or more adhesive layers of Examples 27–32. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity. One reason for this was the much stronger seal between the adhesive layer and the person's teeth than is possible when using the bleaching gel and the dental tray only. Another reason was that the strong adhesion between the adhesive layer and the person's teeth greatly diminished the freedom of movement of the bleaching device relative to the person's teeth.

Example 34

A dental bleaching gel suitable for use in manufacturing dental bleaching compositions and devices according to the invention was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The resulting dental bleaching gel was extremely thick. The dental bleaching gel was used to form dental bleaching devices according to the invention by being placed adjacent to one or more adhesive layers of Examples 27–32. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 35

A dental bleaching gel suitable for use in manufacturing dental bleaching compositions and devices according to the invention was formed by mixing together the following components:

| | |
|---|---|
| Water | 18% |
| Edetate Disodium | 0.1% |
| Carbamide Peroxide | 18.5% |

| | |
|---|---|
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 27–32. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 36

A dental bleaching gel suitable for use in manufacturing dental bleaching compositions and devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 27–32. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 37

A dental bleaching gel suitable for use in manufacturing dental bleaching compositions and devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 27–32. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 38

Any of the dental bleaching gels of Examples 33–37 are placed adjacent to an in surface of any of the adhesive layers of Examples 1–32 in order to form dental bleaching compositions and devices according to the invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An article of manufacture for use in bleaching a person's teeth, comprising:
a shaped dental bleaching composition having a tray-like configuration comprising a front side wall, a rear side wall, and a trough between said front and rear side walls, the dental bleaching composition further comprising:
an adhesive layer comprising a substantially solid adhesive composition that has increased adhesiveness to teeth when moistened by saliva or water, said adhesive composition comprising at least one tooth adhesion agent that at least partially contributes to said increased adhesiveness to teeth, and said adhesive layer having sufficient rigidity to substantially maintain the adhesive layer in said tray-like configuration so that it is adapted for handling and placement onto the teeth; and
a dental bleaching gel, adjacent to an inner surface of said adhesive layer, comprising at least one dental bleaching agent, at least one tackifying agent, and a liquid or gel carrier.

2. An article of manufacture as defined in claim 1, said dental bleaching composition being initially horseshoe shaped prior to use so that said bleaching composition at least approximately conforms to a person's dental arch with minimal longitudinal shaping.

3. An article of manufacture as defined in claim 1, said dental bleaching composition initially having a longitudinal curvature that is less than the curvature of a person's dental arch prior to use so that additional longitudinal curving of said bleaching composition is required when said bleaching composition is placed over a person's teeth.

4. An article of manufacture as defined in claim 1, said dental composition initially having a substantially straight longitudinal profile prior to use so that longitudinal curving of said bleaching composition is required when said bleaching composition is placed over a person's teeth.

5. An article of manufacture as defined in claim 1, at least a portion of said trough having an approximate U-shaped cross section.

6. An article of manufacture as defined in claim 1, at least a portion of said trough having an approximate V-shaped cross section.

7. An article of manufacture as defined in claim 1, at least a portion of said trough having an approximate L-shaped cross section.

8. An article of manufacture as defined in claim 1, at least a portion of said trough having approximately a rectangular or trapezoidal cross section.

9. An article of manufacture as defined in claim 1, said bleaching composition sized and configured so as to fit over at least a portion of a person's upper dental arch.

10. An article of manufacture as defined in claim 1, said bleaching composition sized and configured so as to fit over at least a portion of a person's lower dental arch.

11. An article of manufacture as defined in claim 1, wherein said bleaching composition is sized and configured so as to approximately terminate at or near a person's gingival margin when said bleaching composition is in use.

12. An article of manufacture as defined in claim 1, said tooth adhesion agent comprising polyvinyl pyrrolidone.

13. An article of manufacture as defined in claim 1, said tooth adhesion agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

14. An article of manufacture as defined in claim 1, said tooth adhesion agent having a concentration in a range of about 10% to about 90% by weight of said adhesive composition.

15. An article of manufacture as defined in claim 1, said tooth adhesion agent having a concentration in a range of about 20% to about 80% by weight of said adhesive composition.

16. An article of manufacture as defined in claim 1, said tooth adhesion agent having a concentration in a range of about 40% to about 75% by weight of said adhesive composition.

17. An article of manufacture as defined in claim 1, said adhesive composition further comprising at least one humectant.

18. An article of manufacture as defined in claim 1, wherein said adhesive layer has a cross-sectional thickness in a range of about 0.1 mm to about 0.5 mm.

19. An article of manufacture as defined in claim 1, wherein said adhesive layer has a cross-sectional thickness in a range of about 0.5 mm to about 2 mm.

20. An article of manufacture as defined in claim 1, wherein said adhesive layer has a cross-sectional thickness in a range of about 2 mm to about 3 mm.

21. An article of manufacture as defined in claim 1, said adhesive composition further comprising at least one member selected from the group comprising dental bleaching agents, dental desensitizing agents, remineralizing agent, antimicrobial agents, antiplaque agents, and anti-tartar agents.

22. An article of manufacture as defined in claim 1, said dental bleaching gel further comprising at least one member selected from the group comprising dental desensitizing agents, remineralizing agent, antimicrobial agents, antiplaque agents, and anti-tartar agents.

23. An article of manufacture as defined in claim 1, said dental bleaching agent having a concentration in a range of about 1% to about 60% by weight of said dental bleaching gel.

24. An article of manufacture as defined in claim 1, said dental bleaching agent having a concentration in a range of about 3% to about 40% by weight of said dental bleaching gel.

25. An article of manufacture as defined in claim 1, said dental bleaching agent having a concentration in a range of about 5% to about 30% by weight of said dental bleaching gel.

26. An article of manufacture as defined in claim 1, said tackifying agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

27. An article of manufacture as defined in claim 1, further comprising a barrier layer comprising a moisture-resistant material adjacent to an outer surface of said adhesive layer that protects the dental bleaching composition from saliva or moisture when in use.

28. An article of manufacture as defined in claim 27, said barrier layer being flexible so that it will readily conform to the shape of a person's teeth when in use.

29. An article of manufacture as defined in claim 27, said barrier layer comprising at least one polyolefin.

30. An article of manufacture as defined in claim 29, said polyolefin comprising at least one of polyethylene, high density polyethylene, low density polyethylene, ultra-low density polyethylene, polypropylene, or polytetrafluoroethylene.

31. An article of manufacture as defined in claim 27, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

32. An article of manufacture as defined in claim 27, said barrier layer having a cross-sectional thickness in a range of about 0.025 mm to about 1.5 mm.

33. An article of manufacture as defined in claim 27, said barrier layer having a cross-sectional thickness in a range of about 0.05 mm to about 1 mm.

34. An article of manufacture as defined in claim 1, further comprising a sealed package within which said bleaching composition is sealed prior to use.

35. A kit for use in desensitizing a person's teeth comprising a plurality of said shaped dental bleaching compositions according to claim 1.

36. A kit as defined in claim 35, wherein at least some of said shaped dental bleaching compositions are stacked and internested together.

37. A kit as defined in claim 35, further comprising a barrier layer, or a material used to make a barrier layer, that is positioned adjacent to an outer surface of the adhesive layer when the dental bleaching composition is in use.

38. A method for bleaching a person's teeth comprising obtaining a dental bleaching composition according to claim 1 and placing said bleaching composition over at least a portion of the person's teeth for a desired time period.

39. An article of manufacture for use in bleaching a person's teeth, comprising:
a barrier layer comprising a moisture-resistant material in the shape of a dental tray comprising a front side wall, a rear side-wall, and a trough between said front and rear side walls; and
a dental bleaching composition within said trough comprising:

an adhesive layer, adjacent to said barrier layer, comprising a substantially solid adhesive composition that has increased adhesiveness to teeth when moistened by saliva or water, said adhesive composition comprising at least one tooth adhesion agent that at least partially contributes to said increased adhesiveness to teeth, and said adhesive layer having sufficient rigidity to substantially maintain the adhesive layer in said tray-like configuration so that it is adapted for handling and placement onto the teeth; and a dental bleaching gel, adjacent to an inner surface of said adhesive layer, comprising at least one dental bleaching agent, at least one tackifying agent, and a liquid or gel carrier.

40. An article of manufacture as defined in claim 39, at least a portion of said trough having a cross section that is approximately U-shaped, V-shaped, L-shaped, rectangular, or trapezoidal.

41. An article of manufacture as defined in claim 39, said barrier layer being flexible so that it will readily conform to the shape of a person's teeth when in use.

42. An article of manufacture as defined in claim 39, said barrier layer comprising at least one polyolefin.

43. An article of manufacture as defined in claim 42, said polyolefin comprising at least one of polyethylene, high density polyethylene, low density polyethylene, ultra-low density polyethylene, polypropylene, or polytetrafluoroethylene.

44. An article of manufacture as defined in claim 39, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

45. An article of manufacture as defined in claim 39, said barrier layer having sufficiently rigidity so as to at least partially contribute to maintaining itself in the shape of a dental tray prior to use.

46. An article of manufacture as defined in claim 45, said barrier layer comprising a customized dental tray.

47. An article of manufacture as defined in claim 39, said barrier layer comprising a thin, flexible membrane having no predefined shape, said adhesive layer having sufficiently rigidity so as to at least partially contribute to maintaining said barrier layer in the shape of a dental tray prior to use.

48. An article of manufacture as defined in claim 39, said trough being initially horseshoe shaped prior to use so that said dental desensitizing device at least approximately conforms to a person's dental arch with minimal longitudinal shaping.

49. An article of manufacture as defined in claim 39, said front side wall, rear side wall, and trough initially having a longitudinal curvature that is less than the curvature of a person's dental arch prior to use so that additional longitudinal curving is required when said dental bleaching composition is placed over a person's teeth.

50. An article of manufacture as defined in claim 39, said front side wall, rear side wall, and trough initially having a substantially straight longitudinal profile prior to use so that longitudinal curving of is required when said dental bleaching composition is placed over a person's teeth.

51. An article of manufacture as defined in claim 39, said tooth adhesion agent comprising polyvinyl pyrrolidone.

52. An article of manufacture as defined in claim 39, said adhesive composition further comprising at least one member selected from the group comprising dental bleaching agents, dental desensitizing agents, remineralizing agent, antimicrobial agents, antiplaque agents, and anti-tartar agents.

53. An article of manufacture as defined in claim 39, said dental bleaching gel further comprising at least one member selected from the group comprising dental desensitizing agents, remineralizing agent, antimicrobial agents, antiplaque agents, and anti-tartar agents.

54. A kit for use in desensitizing a person's teeth comprising a plurality of dental bleaching devices, each comprising the barrier layer and dental bleaching composition of claim 39.

55. A method for desensitizing a person's teeth comprising obtaining a dental bleaching device comprising the barrier layer and dental bleaching composition of claim 39 and then placing said dental bleaching device over at least a portion of the person's teeth for a desired time period.

56. A dental bleaching device in the shape of a dental tray suitable for placement over a person's teeth in order to carry out dental bleaching, comprising:

a thin, flexible barrier layer comprising a moisture-resistant material;

an adhesive layer adjacent said barrier layer and comprising a substantially solid adhesive composition in the shape of a dental tray comprising a front side wall, a rear side wall, and a trough between said front and rear side walls, said adhesive layer having a rigidity so that said adhesive layer contributes more to maintaining said dental bleaching device in the shape of a dental tray prior to use than said barrier layer, said adhesive comprising at least one tooth adhesion agent that provides or contributes to increased adhesiveness when said adhesive composition is moistened by saliva or water; and a dental bleaching gel adjacent to an inner surface of said adhesive layer and comprising a dental bleaching agent, a tackifying agent, and a liquid or gel carrier.

57. A dental bleaching device as defined in claim 56, at least a portion of said trough having a cross section that is approximately U-shaped, V-shaped, L-shaped, rectangular, or trapezoidal.

58. A method of manufacturing a shaped dental bleaching composition, comprising:

mixing together a tooth adhesion agent and a solvent to form an adhesive composition intermediate;

removing at least a portion of said solvent from said adhesive composition intermediate so as to form an adhesive layer comprising a substantially solid adhesive composition having increased adhesiveness to teeth when moistened with saliva or water, and said adhesive layer having sufficient rigidity to substantially maintain the adhesive layer in a tray-like configuration so that it is adapted for handling and placement onto the teeth; and placing a dental bleaching gel adjacent to an inner surface of the tray-like configuration formed by the adhesive layer.

59. A method as defined in claim 58, further comprising placing or forming a barrier layer adjacent to said adhesive layer.

60. A method as defined in claim 59, wherein said barrier layer comprises a dental tray.

* * * * *